United States Patent
Spears et al.

(10) Patent No.: US 10,154,670 B2
(45) Date of Patent: Dec. 18, 2018

(54) **COMPOSITIONS COMPRISING *BACILLUS* STRAINS AND METHODS OF USE TO SUPPRESS THE ACTIVITIES AND GROWTH OF FUNGAL PLANT PATHOGENS**

(71) Applicant: Bio-Cat Microbials LLC, Shakopee, MN (US)

(72) Inventors: Jessica Spears, Minnetonka, MN (US); Steve C. Lamb, Shakopee, MN (US); Sebhat Gebrechristos, New Hope, MN (US); Christopher Schuler, Charlottesville, VA (US)

(73) Assignee: BIO-CAT MICROBIALS LLC, Shakopee, MN (US)

( * ) Notice: Subject to any disclaimer, the term of this patent is extended or adjusted under 35 U.S.C. 154(b) by 0 days.

(21) Appl. No.: 14/911,971

(22) PCT Filed: Aug. 12, 2014

(86) PCT No.: PCT/US2014/050710
§ 371 (c)(1),
(2) Date: Feb. 12, 2016

(87) PCT Pub. No.: WO2015/023662
PCT Pub. Date: Feb. 19, 2015

(65) Prior Publication Data
US 2016/0192660 A1    Jul. 7, 2016

Related U.S. Application Data

(60) Provisional application No. 62/016,855, filed on Jun. 25, 2014, provisional application No. 61/958,994, filed on Aug. 12, 2013.

(51) Int. Cl.
*A01N 63/00* (2006.01)
*C12Q 1/18* (2006.01)
*C12N 1/20* (2006.01)

(52) U.S. Cl.
CPC ............... *A01N 63/00* (2013.01); *C12N 1/20* (2013.01); *C12Q 1/18* (2013.01)

(58) Field of Classification Search
None
See application file for complete search history.

(56) References Cited

U.S. PATENT DOCUMENTS

| | | |
|---|---|---|
| 6,878,179 B2 | 4/2005 | Porubacan |
| 2003/0045428 A1 | 3/2003 | Porubcan |
| 2011/0027232 A1 | 2/2011 | Herman et al. |
| 2012/0003197 A1 | 1/2012 | Jackobsen et al. |

FOREIGN PATENT DOCUMENTS

| | | |
|---|---|---|
| WO | 96/39840 | 12/1996 |
| WO | WO 98/21964 | 5/1998 |
| WO | 2013/050867 | 4/2013 |

OTHER PUBLICATIONS

Shida ("Proposal for Two new Genera, *Brevibacillus* gen. nov. and *Aneurinibacillus* gen. nov" International Journal of Systematic Bacteriology, Oct. 1996, vol. 46 No. 4, 939-946).*
Castillo, et al. "Biological Control of Root Pathogens by Plant Growth Promoting *Bacillus* spp." Weed and Pest Control—Conventional and New Challenges Chapter 4 (2013).
International Search Report for PCT/US2014/050710 dated Dec. 15, 2014.
Written Opinion for PCT/US2014/050710 dated Dec. 15, 2014.
Rincon-Vitova Insectories, Inc, Information Sheet—Rhizoboost Bacterial Soil Inoculant for Restoring, downloaded Jun. 18, 2018 from the internet at http://www.rinconvitova.com/Rhizoboost_rvi.pdf, 2 pages total.
Yobo et al., "Effect of commerically available rhizobacteria strains on growth and production of lettuce, tomato and pepper," South African Journal of Plant and Soil, 2004, vol. 21(4), pp. 230-235.

* cited by examiner

Primary Examiner — Robert J Yamasaki
Assistant Examiner — Charles Zoltan Constantine
(74) *Attorney, Agent, or Firm* — Arent Fox LLP

(57) ABSTRACT

This invention provides compositions of *Bacillus* strains and methods for using such compositions to inhibit the activity and/or growth of fungal pathogens of plants. In one embodiment, this invention provides a composition comprising *Bacillus* bacteria selected from the group consisting of *Brevibacillus laterosporus* strain CM-3, *Brevibacillus laterosporus* strain CM-33, *Bacillus amyloliquefaciens* BCM-CM5, *Bacillus licheniformis* ATCC-11946, *Bacillus mojavensis* BCM-01, *Bacillus pumilus* NRRL-1875, *Bacillus subtilis* 10 DSM-10, *Bacillus subtilis* NRRL-1650, *Bacillus megaterium* BCM-07, *Paenibacillus polymyxa* DSM-36, *Paenibacillus chitinolyticus* DSM-11030, and combinations thereof. In another embodiment, this invention provides a method for preparing a bacterial composition comprising one or more *Bacillus* strains by growing *Bacillus* strain bacteria until the bacteria form spores, collecting said spores, and formulating said composition.

25 Claims, 22 Drawing Sheets

A
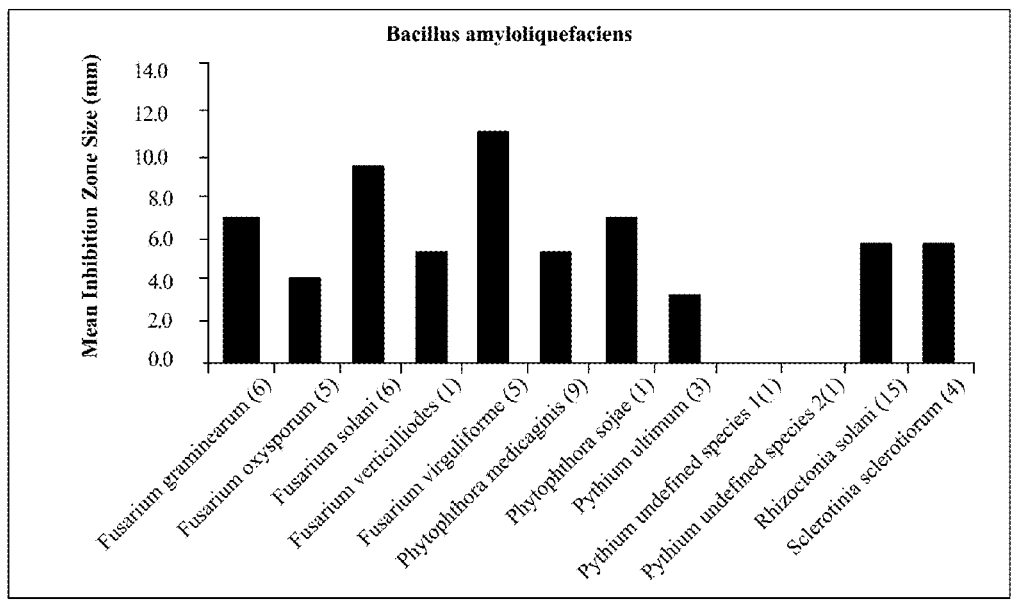
B
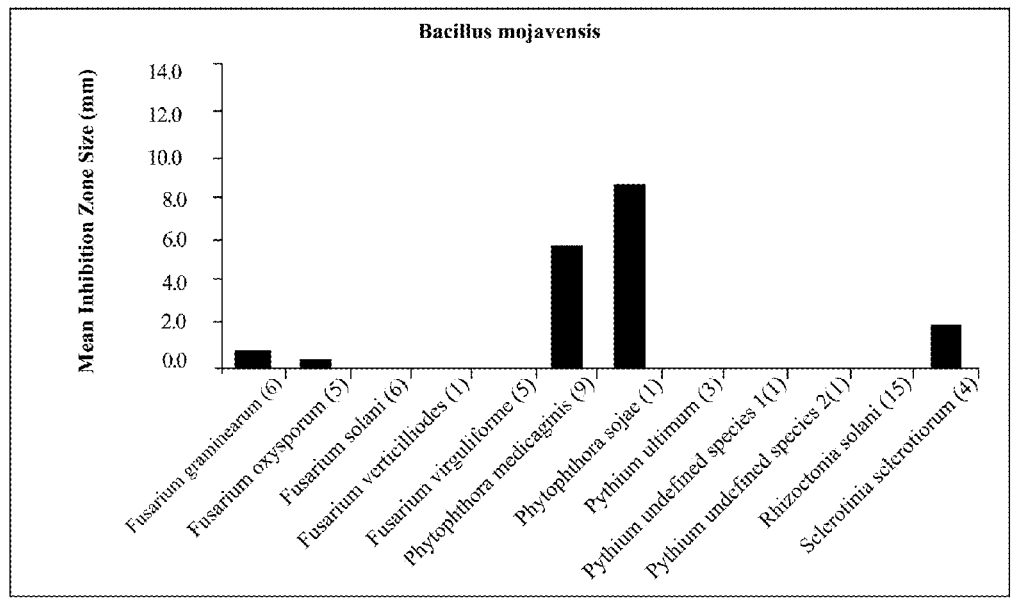
FIG. 2A-B

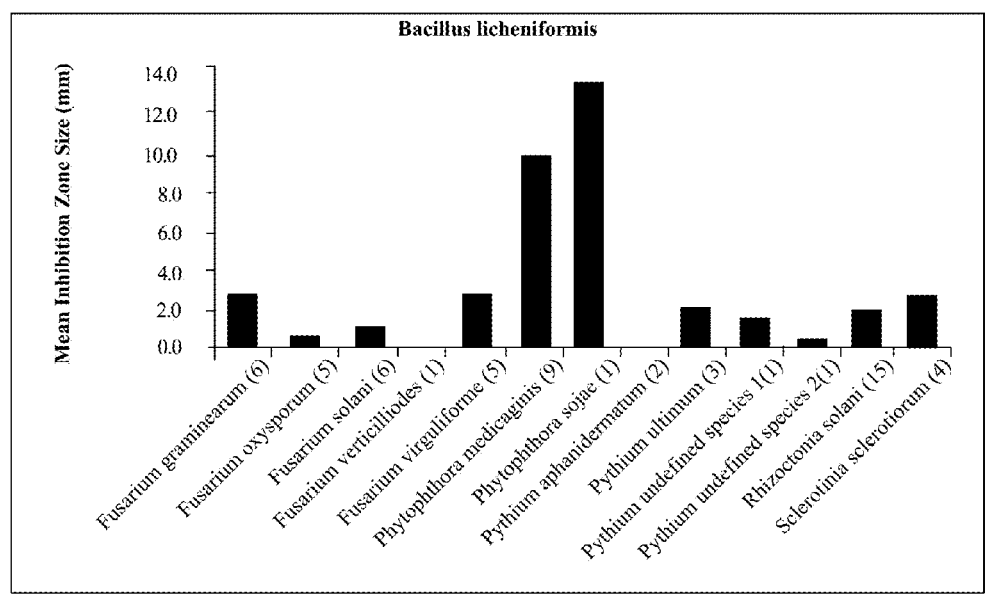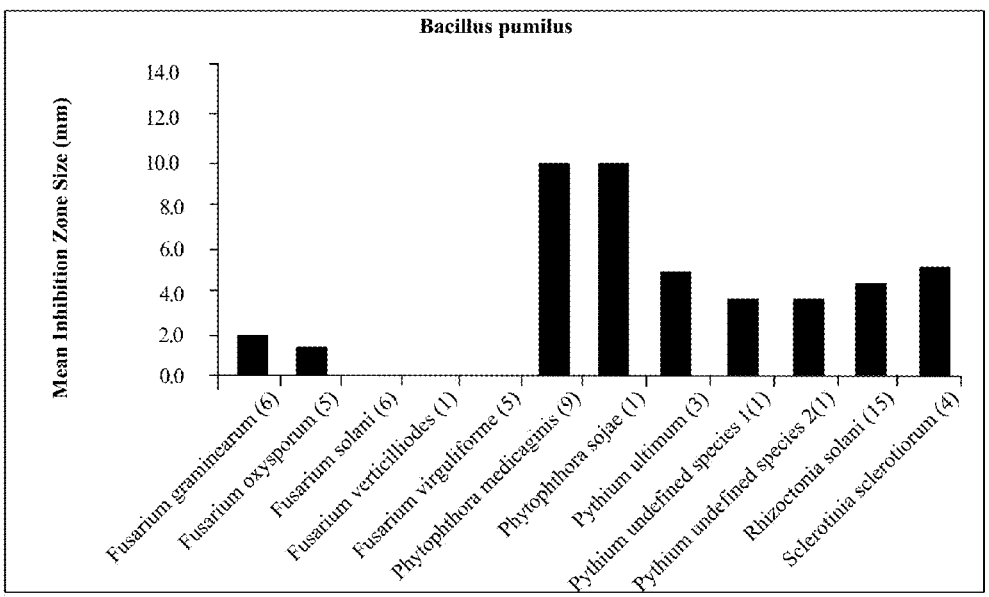
FIG. 2C-D

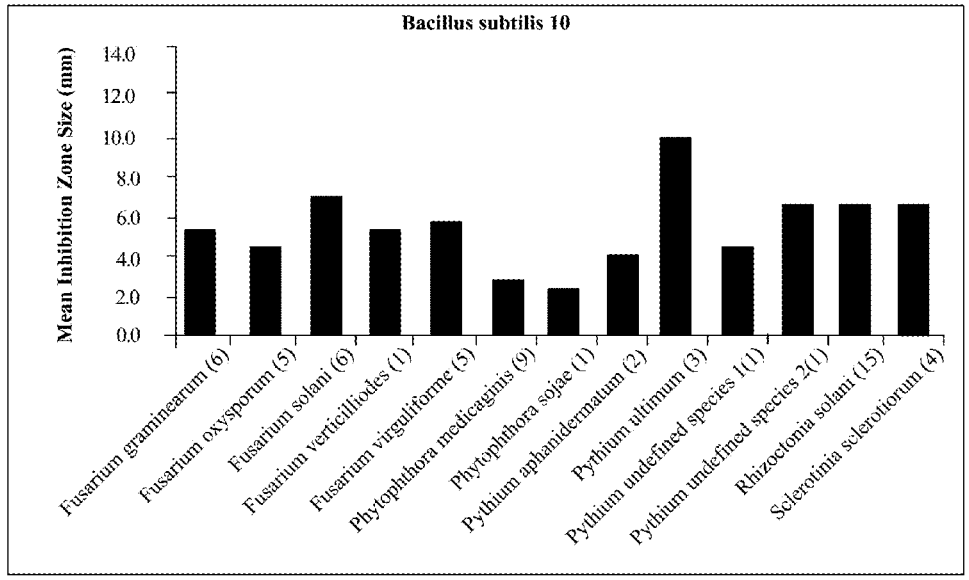
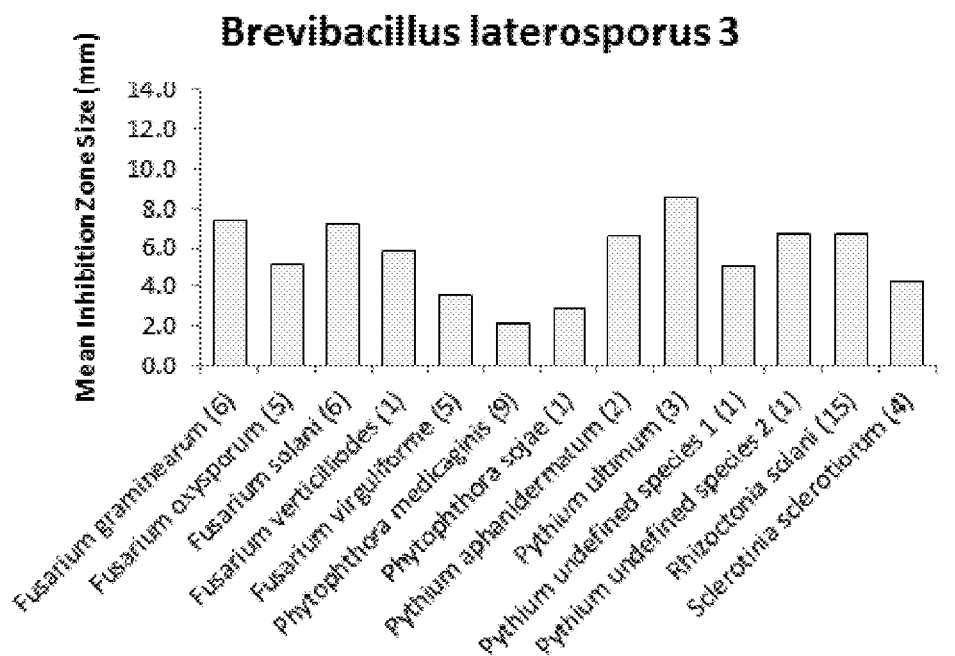
FIG. 2E-F

G
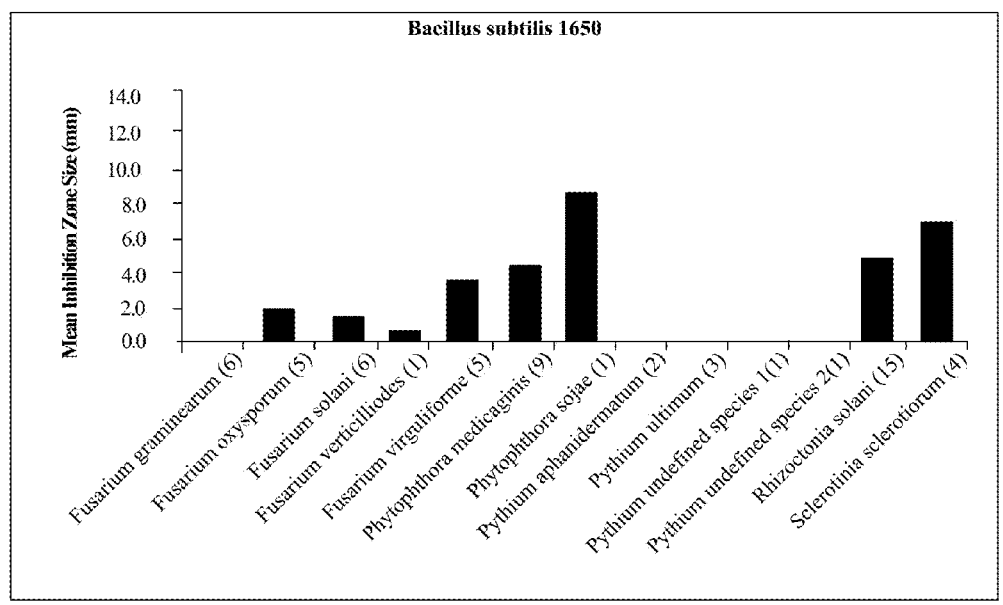
H
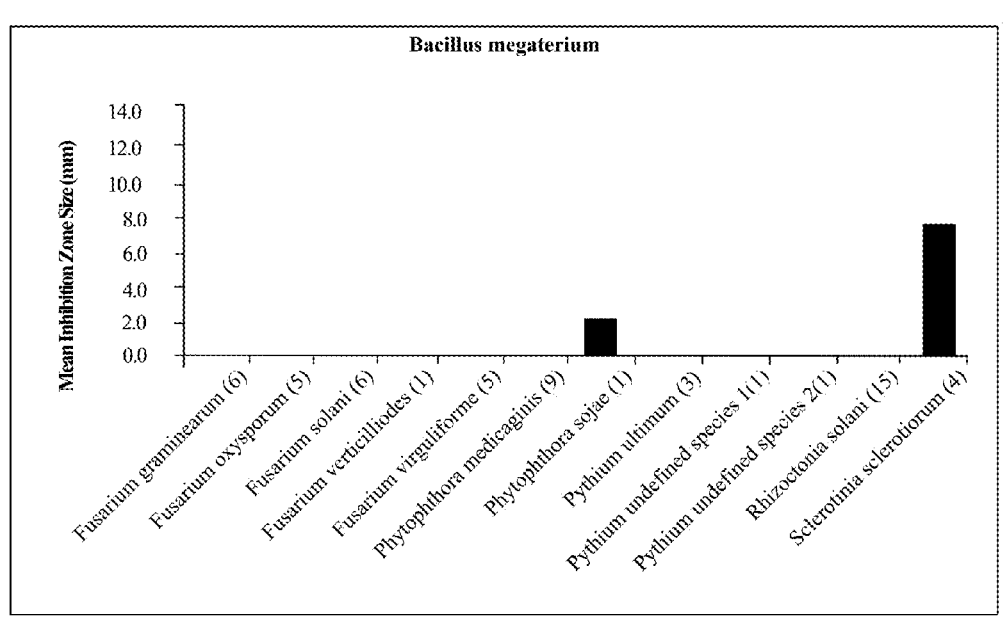
FIG. 2G-H

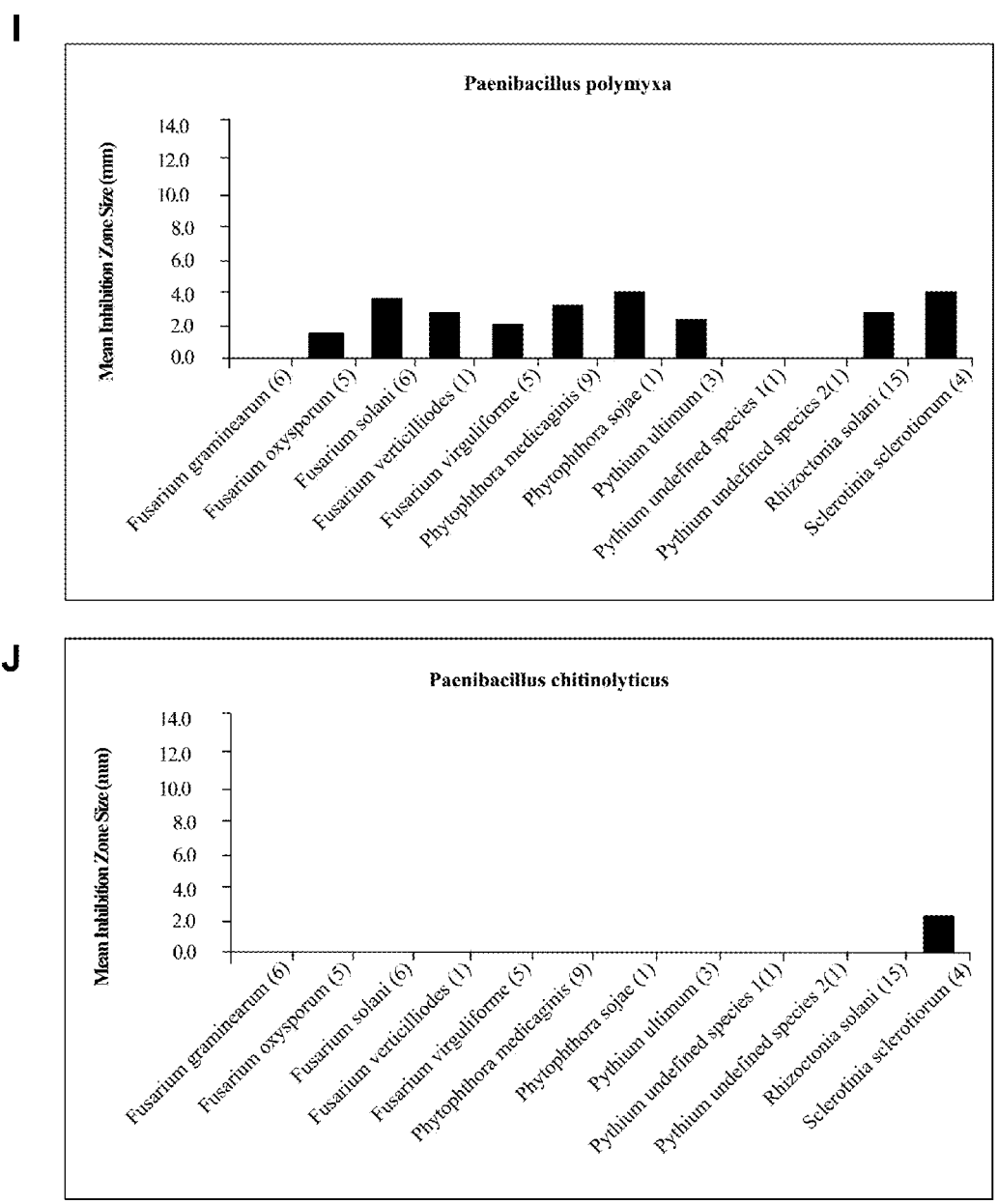
FIG. 2I-J

A
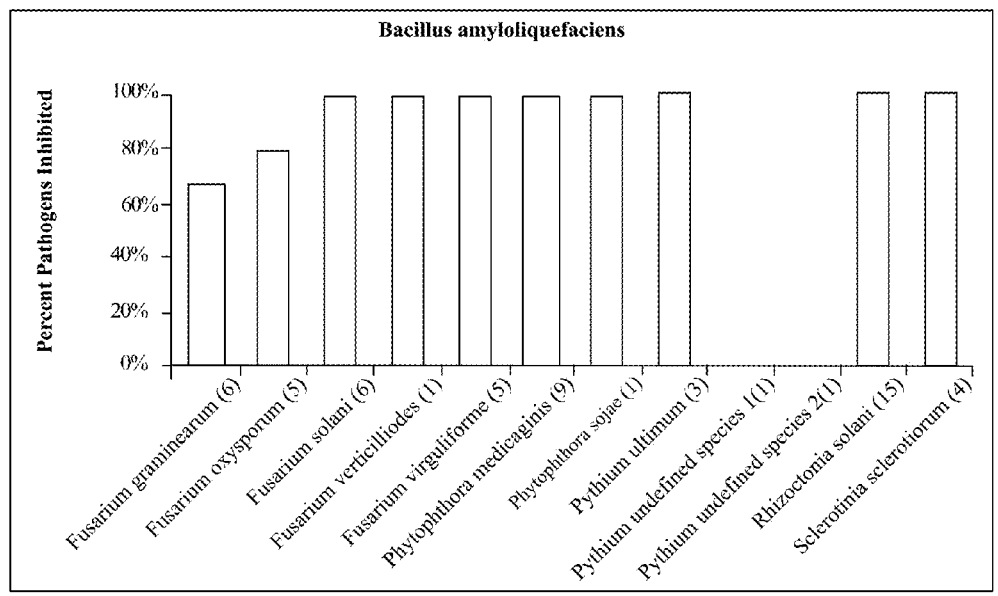
B
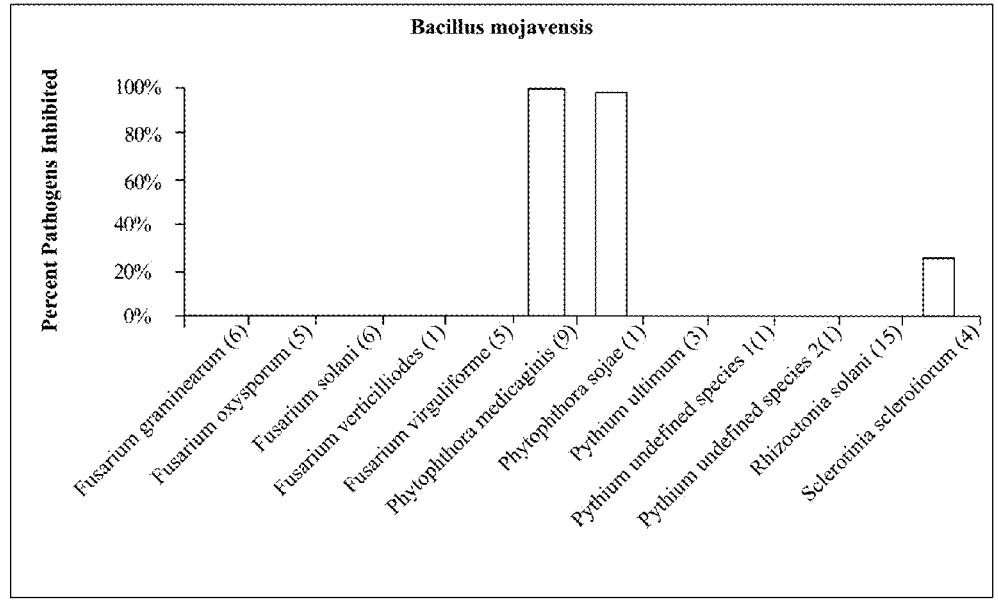
FIG. 3A-B

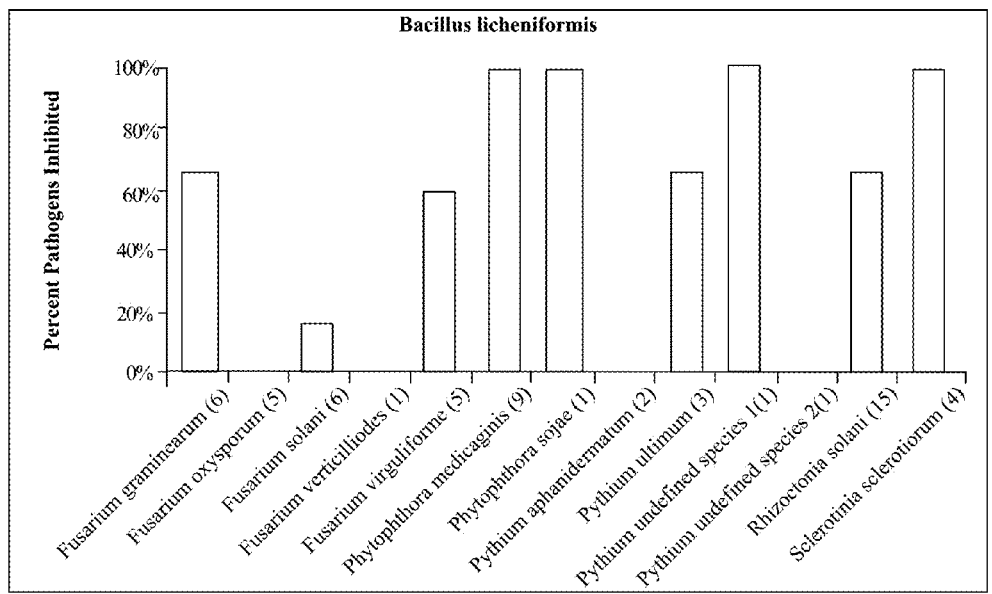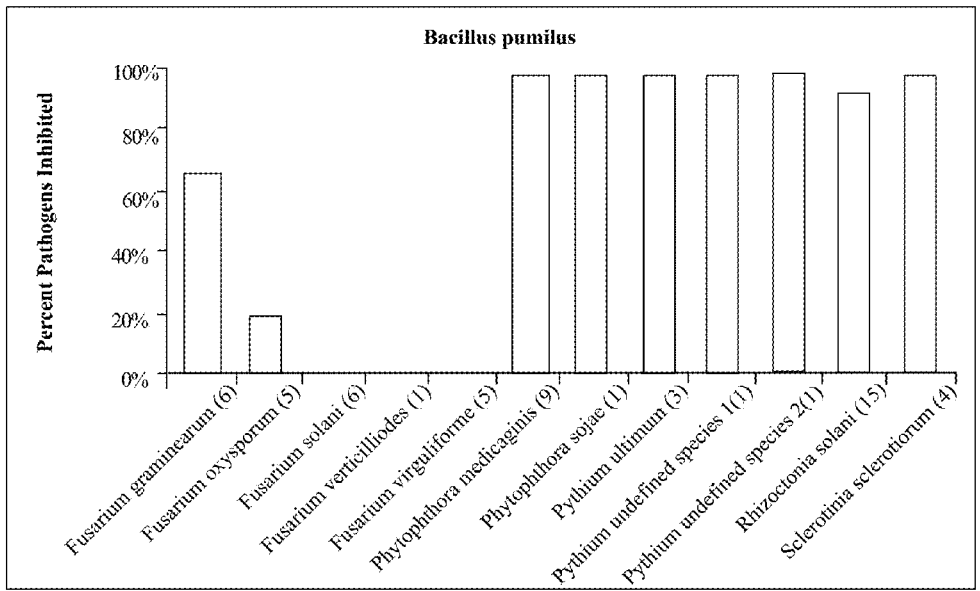
FIG. 3C-D

E
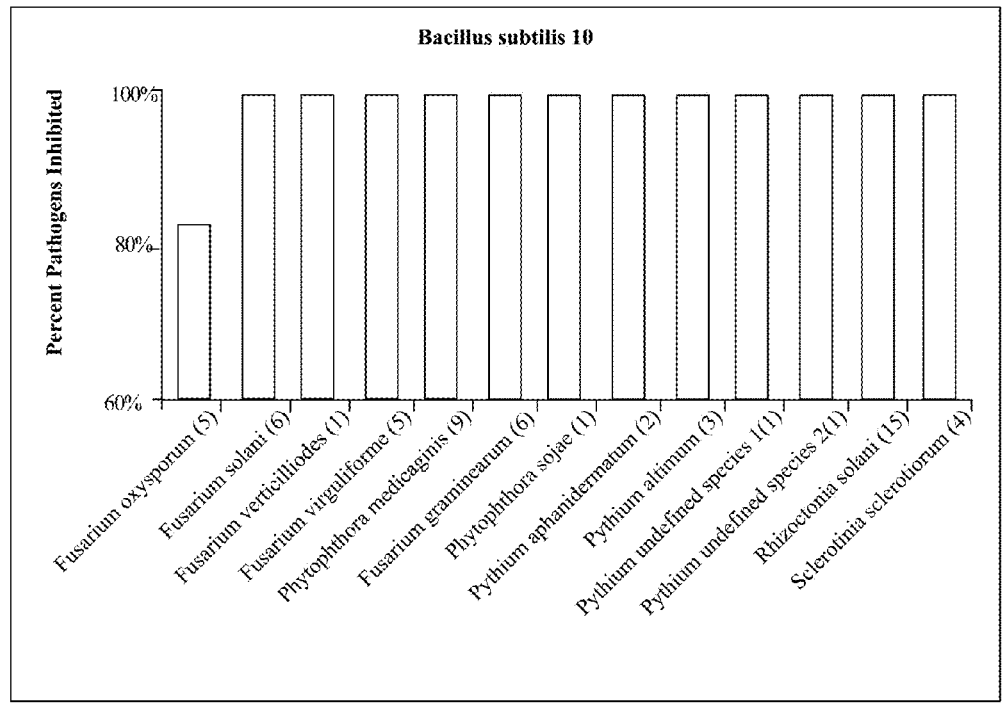
F
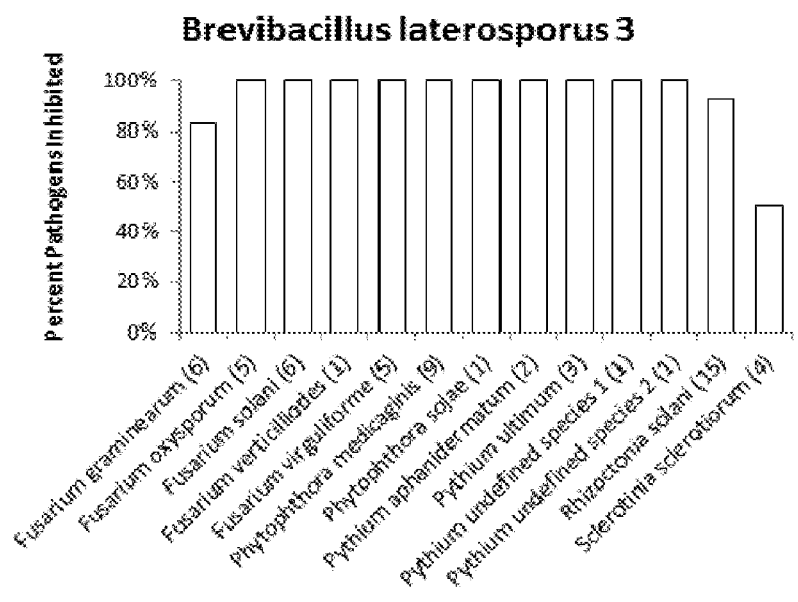
FIG. 3E-F

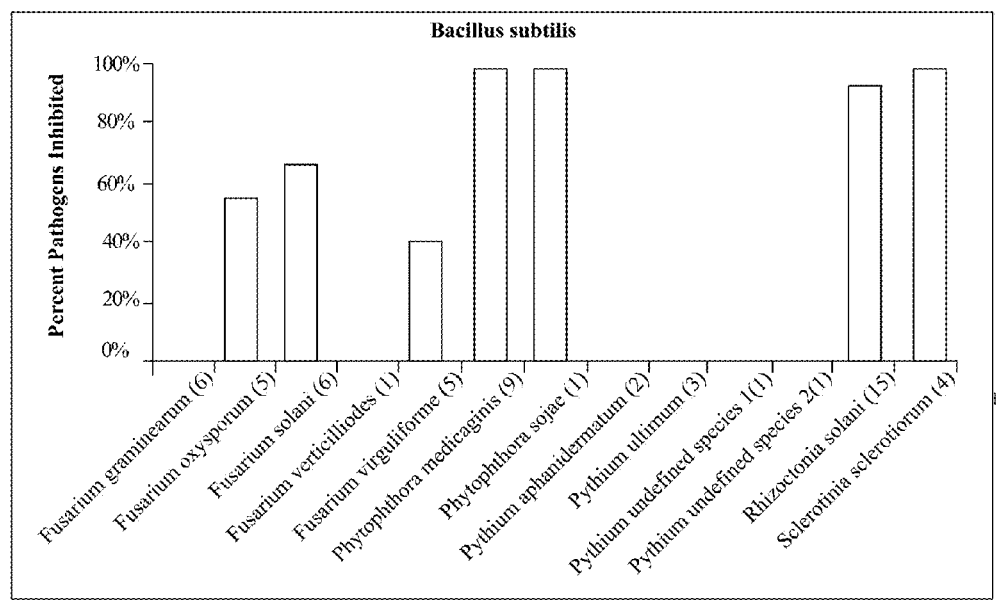
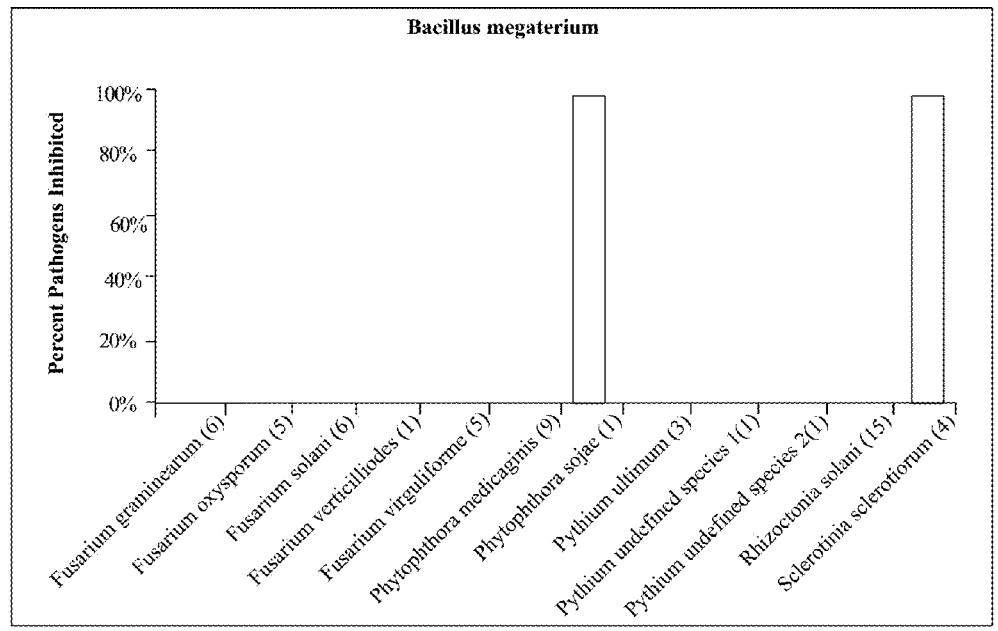
FIG. 3G-H

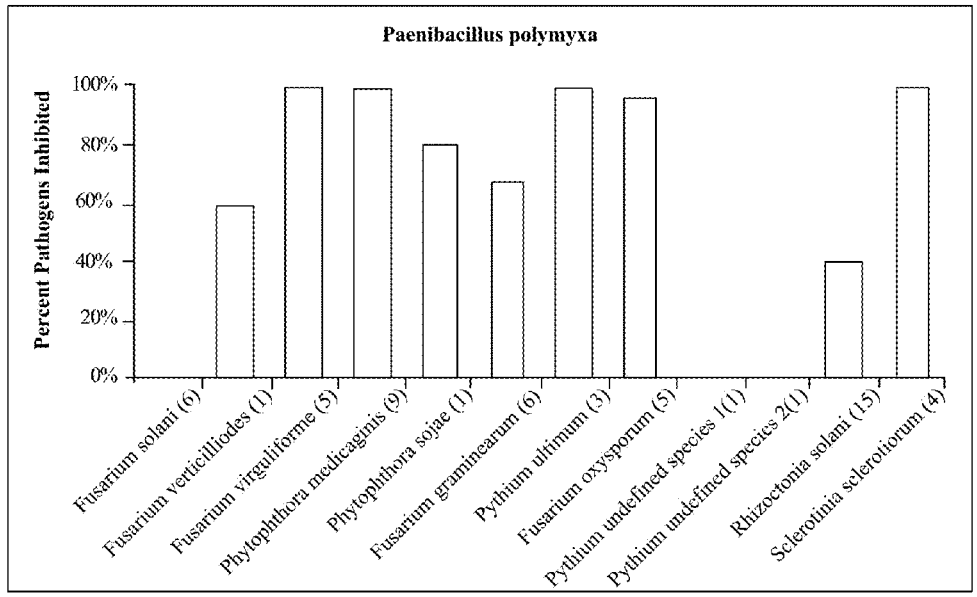
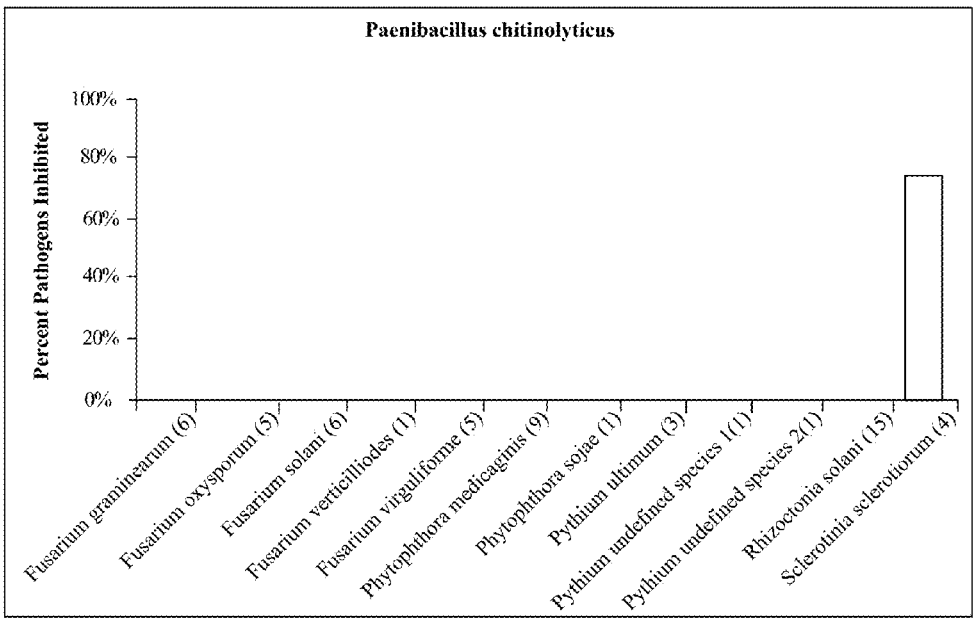
FIG. 3I-J

A
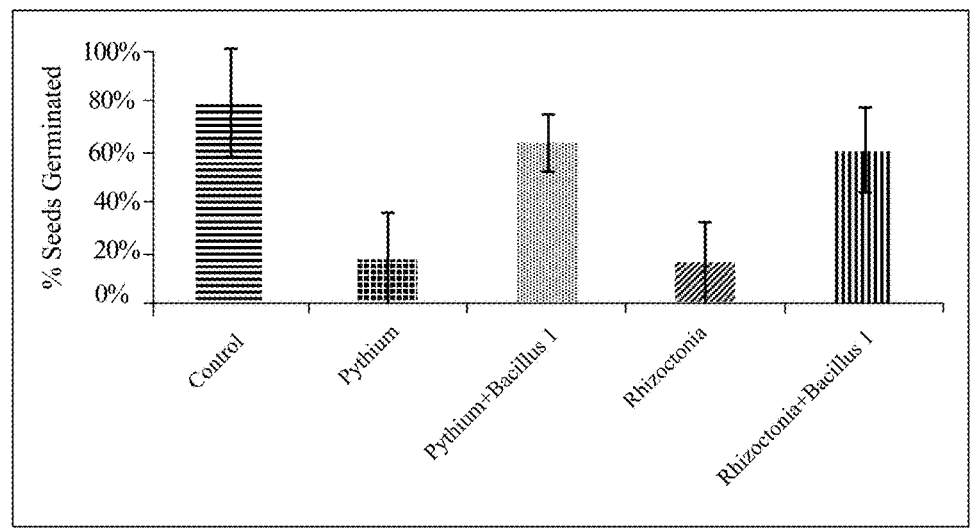
B
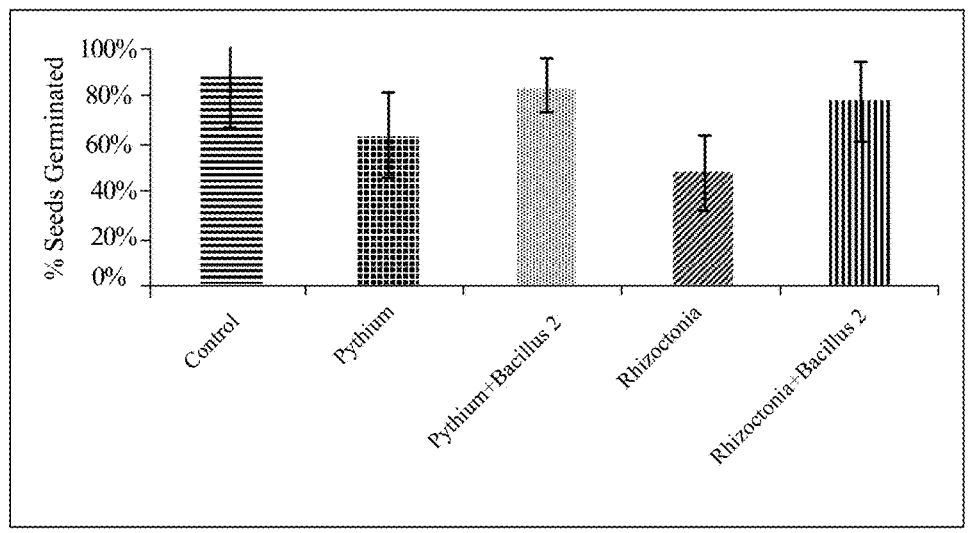
FIG. 12A-B

COMPOSITIONS COMPRISING *BACILLUS* STRAINS AND METHODS OF USE TO SUPPRESS THE ACTIVITIES AND GROWTH OF FUNGAL PLANT PATHOGENS

CROSS-REFERENCE TO RELATED APPLICATIONS

This application is a U.S. National Phase Filing of International Patent Application PCT/US14/50710 filed Aug. 12, 2014, which claims the benefit of priority to U.S. Provisional Patent Application 62/016,855, filed Jun. 25, 2014, and which claims the benefit of priority to U.S. Provisional Patent Application No. 61/958,994, filed Aug. 12, 2013, the contents of each are hereby incorporated by reference in their entireties.

FIELD OF THE INVENTION

The present invention is directed to the use of a mixture of *Bacillus* strain concentrates to inhibit the activities and growth of plant pathogens.

BACKGROUND OF THE INVENTION

The use of viable microorganisms as root-zone inoculants, particularly beneficial bacteria, has expanded to include many food crops including fruits, vegetables, root crops and grains. The emerging science, referred to as probiotics, is based in part on the observation that certain soils, which contain specific cultures of microorganisms that aggressively colonize root surfaces, suppress a variety of plant diseases. It is postulated that colonization of root surfaces with deleterious microorganisms can be prevented by pre-colonization with probiotic microorganisms, which is referred to as competitive exclusion (CE). Schroth, et al. (1982) entitled "Disease-Suppressive Soil and Root-Colonizing Bacteria", Science, Vol. 216: 1376-1381 (1982). In this review, gram-negative *Pseudomonas* bacterial species were discussed as being the most effective in CE, and their ability to produce iron-binding compounds (called "siderophores") was postulated as the potential mode-of-action.

U.S. Pat. No. 5,503,651 discusses plant growth promoting rhizobacteria (referred to therein as "PGPR"), and in a listing of 41 PGPR bacterial species, 37 of them are *Pseudomonas* species and strains. Since strains of these same *Pseudomonas* species are plant pathogens, and since plasmid transfer within a bacterial species is commonplace, there is a concern that there could be transfer of genetic material from a pathogenic strain, to convert a previously harmless strain into a pathogenic strain. Accordingly, it is preferred to use gram-positive bacteria, such as *Bacillus*, and not gram-negative *Pseudomonas*, for probiotics.

U.S. Pat. No. 4,877,738 discusses a seed inoculum for application to seeds to be protected from "damping off" fungal plant disease, and this patent also discusses a method of protecting growing plants from damping off and root rot fungal plant disease with a similar composition. The composition includes a carrier and an effective quantity of protective bacteria, including *Bacillus cereus* ATCC 53522, a mutant of *Bacillus cereus* ATCC 53522 retaining the capability to produce a plant protecting toxin effective against *Phytophthora megasperma*, a mixture of such mutants, and a mixture of *Bacillus cereus* ATCC 53522 and such mutants wherein the inoculum is substantially soil-free. There is no indication that testing of any other *Bacillus* species for such purposes had the same effect.

U.S. Pat. No. 4,952,229 discusses a microbial plant supplement and method for increasing plant productivity and quality, which includes a mixture of microbes with various in vivo properties. This patent also states that the microbes should be used with certain organic acids, and with trace metals and minerals.

U.S. Pat. No. 4,952,229 describes commercialization hurdles for mixtures of microbial strains, because it would be difficult and expensive to insure uniform end-products due to the difficulties associated with consistently combining a plurality of microorganisms. Without a consistent and uniform end-product, it would be difficult to obtain the regulatory permits required for sales and marketing of such products. It is indicated to be preferable for a single strain of a single species is the only active ingredient in a commercial product.

U.S. Pat. No. 5,441,735 discusses the use of the microorganism *Erwina carotovora* subsp. *carotovora* (E234M403 strain) which has been modified by mutagenesis to eliminate its soft rot pathology in rice. When applied to rice plants, this modified strain competitively excludes pathogenic strains of the same species. The disadvantage with this strain is the same as discussed above with *Pseudomonas*, i.e., a reversion to pathology is possible since this microorganism is pathogenic prior to mutation. Also, it is clear that this microorganism is of no benefit to rice that is not experiencing a soft rot infection.

U.S. Pat. No. 5,157,207 discusses a method of inoculating bacteria into rice by introducing a bacterial cell into the seed or plant, such bacteria belonging to the species *Calvibacter xyli*. This creates a modified rice plant that demonstrates a slight yield improvement (4.81 kg/ha treated vs. 4.66 kg/ha control). Microbial invasion into rice plant tissue is not preferred, however, as it raises possible health and regulatory concerns.

There is a need for new enhancing yields in rice farming beyond those achieved with modern "high yielding" rice varieties. From 1964 to 1990, irrigated rice field yields in Asia increased from 3.0 to 5.8 metric tons/ha. This was largely the result of the introduction of the higher yielding IR varieties of rice developed by the International Rice Research Institute in the Philippines, starting with IR-8 in 1966. At the time of introduction, IR-8 yielded 10 metric tons/ha in the Philippines and up to 14 metric tons/ha in certain temperate regions of China, where fewer overcast days resulted in enhanced photosynthesis. Yields from variety IR-8, as well as other IR varieties, have decreased at a rate of 0.2 metric tons/ha/yr. Pingali, et al., C.A.B. International & International Rice Research Institute (1997), "Asian rice bowls: The returning crisis?" New York: CAB International. Yields of 6 metric tons/ha are seldom achieved by Asian farmers. New rice varieties are being selected more for disease resistance, shorter photoperiod, and grain quality than for yield. It has become generally accepted within the industry that yield increases from advances in plant genetics have been effectively maximized, and further increases can only be achieved by other means. A similar need exists for other crops due to pressures on the environment and increased demand for food production.

Tomato-Tone® (plant fertilizer) made by Esporma comprises a fertilizer and *Bacillus* species bacteria for use as an organic fertilizer. Serenade® Garden Disease Control (antifungal spray for plants) contains *Bacillus subtilis*, a soil-dwelling bacterium that controls leaf blight, black mold, powdery mildew and many other diseases. However, both products contain relatively low amounts of *Bacillus* and are designed for small-scale use.

Serenade® (microbial control agent) is a microbial biological control agent comprising *Bacillus subtilis* strain QST 713 which protects against fungal and bacterial plant pathogens. *Bacillus subtilis* strain QST 713 is a naturally occurring widespread bacterium that can be used to control plant diseases including blight, scab, gray mold, and several types of mildew. SERENADE SOIL® (biofungicide) is a fungicide designed to protect young plants against the effects of soil diseases like *Pythium, Rhizoctonia, Fusarium* and *Phytophthora*.

Annual crop losses due to pre- and post-harvest fungal diseases exceed $260 Billion annually. About 15,000 fungal species cause disease in plants. The majority of these fungal plant pathogens belong to the *Ascomycetes* and *Basidiomycetes*. González-Fernandez, et al. *Journal of Biomedicine and Biotechnology* Vol. 2010, Article ID 932527, 26 pages, 2010. Plant pathogens can have many devastating effects on a variety of commercial crops. Thus there exists in the art a need for compositions and methods for controlling plant fungal pathogens.

SUMMARY OF THE INVENTION

This invention provides compositions of *Bacillus* strains and methods for inhibiting the activity and/or growth of plant fungal pathogens.

In one embodiment, this invention provides a composition comprising *Bacillus* bacteria selected from the group consisting of *Brevibacillus laterosporus* strain CM-3, *Brevibacillus laterosporus* strain CM-33, *Bacillus amyloliquefaciens* BCM-CM5, *Bacillus licheniformis* ATCC-11946, *Bacillus mojavensis* BCM-01, *Bacillus pumilus* NRRL-1875, *Bacillus subtilis* 10 DSM-10, *Bacillus subtilis* NRRL-1650, *Bacillus megaterium* BCM-07, *Paenibacillus polymyxa* DSM-36, *Paenibacillus chitinolyticus* DSM-11030, and combinations thereof. Preferably, the composition comprises at least 1, 2, 3, 4, 5, 6, 7, 8, 9, 10, or 11 of said strains, more preferably the composition comprises at least 2, 3, 4, 5, 6 or 7 of said strains. In one mode of this embodiment, the composition comprises spores or live cells of *Bacillus* strains, preferably the *Bacillus* strain bacteria are in spore form, and the spores may be formulated in a suspension comprising water, which in turn may be substantially chlorine-free. The composition may also comprise nutrient organic compounds, trace minerals, vitamins, growth factors, and/or adjuvants. Typically, the *Bacillus* strain bacteria are in a concentration of $1\times10^3$ to $1\times10^{12}$ colony forming units (CFU)/mL. In one mode of this embodiment, the composition is spray-dried; in another mode, the composition is lyophilized. In another embodiment, the composition is a liquid.

In another embodiment, this invention provides a method for preparing a bacterial composition comprising one or more *Bacillus* strains by growing *Bacillus* strain bacteria until the bacteria form spores, collecting said spores, and formulating said composition. Preferably, the spores are obtained by ultra-filtration, centrifugation, spray-drying, freeze-drying, or combinations thereof. Preferably, the spores will germinate and colonize soil, particularly the rhizosphere.

In yet another embodiment, the invention provides a method for inhibiting the growth and/or activity of fungal plant pathogens comprising applying a bacterial composition comprising one or more *Bacillus* strains to a plant, seed for plant, or soil adjacent to a plant, and the fungal plant pathogens may be members of the *Fusarium* species, optionally *Fusarium graminearum, Fusarium oxysporum, Fusarium solani, Fusarium verticilliodes,* and *Fusarium virguliforme; Phytophthora* species, optionally *Phytophthora medicaginis* and *Phytophthora sojae; Pythium* species, optionally *Pythium aphanidermatum* and *Pythium ultimum, Rhizoctonia* species, optionally *Rhizoctonia solani*; and *Sclerotinia* species, optionally *Sclerotinia sclerotiorum*. The composition may be applied to the soil, to the plant foliage, to the plant seeds, during sowing of the plant seeds, within 10 days of sowing of the plant seeds, optionally within 1, 2, 3, 4, 5, 6, 7, 8, 9, or 10 days of sowing the seeds. The composition may be applied to the soil and/or to the plant foliage after the plants germinate, optionally within 1, 2, 3, 4, 5, 6, 7, 8, 9, or 10 days after germination. The composition may be applied to the soil, to the plant foliage, to the plant seeds, before or after planting or germination. The composition may be applied by seed coating, spraying in planting furrow with seeds, or foliar spray. The composition may be admixed with a soil and then the soil/composition mixture may be applied to the soil, to the plant foliage, to the plant seeds, before or after germination. The composition may be applied after a period of rain or watering of the plants, and preferably, the composition is applied to the plant or soil when the temperature is over 65° F. In one mode of this embodiment, the composition is applied around the seed of the plant. In another mode of this embodiment, the composition is applied by spraying plants or mixing into soil; preferably, the composition is applied to the root zone. The composition is preferably applied within 2 weeks of plant emergence. The composition may be applied within 10 days of sowing of the plant seeds, optionally within 3, 5, or 7 days of sowing the seeds.

Alternatively, the composition is applied after a fungal pathogen is present. In a preferred mode, the composition comprises spores, and the spores germinate and colonize the soil. Typically the composition comprises between at least about $1\times10^3$ to $1\times10^{12}$ CFU/mL.

In still another embodiment, this invention provides a method for increasing the yields of a plant or protecting a plant from fungal pathogens comprising applying the bacterial composition of this invention to the plant, to seeds for the plant or to soil adjacent to the plant. The plant may be a grain crop, optionally barley, sorghum, millet, rice, corn, oats, wheat, barley, or hops. The plant may be an ornamental flower, optionally an annual or perennial; preferably the ornamental flower is a geranium, petunia, or daffodil. The plant may be a legume, optionally alfalfa, clover, peas, beans, lentils, lupins, mesquite, carob, soybeans, peanuts, or tamarind; preferably, the plant is soybean. The plant may be a fruit tree, optionally apple, peach, pear, or plum, or the plant may be a fruit bush, optionally grape, raspberry, blueberry, strawberry, or blackberry. The plant may be a vegetable, optionally tomatoes, beans, peas, broccoli, or cauliflower, or the plant may be a root vegetable, optionally potato, carrot, or beet. The plant may be a decorative tree, optionally poplar, or the plant may be an evergreen tree, optionally pine. The plant may be a vine vegetable, optionally cucumber, pumpkins, or zucchini. In a preferred mode, the composition of this invention comprises *Bacillus* strains which inhibit fungal plant pathogens. Typically, the fungal plant pathogen is a species of the *Fusarium, Phytophthora, Pythium, Rhizoctonia,* or *Sclerotinia* genera; preferably, the fungal plant pathogen is one or more of *Fusarium graminearum, Fusarium oxysporum, Fusarium solani, Fusarium verticilliodes, Fusarium virguliforme, Phytophthora medicaginis, Phytophthora sojae, Pythium aphanidermatum, Pythium ultimum, Rhizoctonia solani,* and/or *Sclerotinia sclerotiorum*. More preferably, substantially all of the fungal plant pathogens are inhibited by one or more of the *Bacillus* strains in the composition. More preferably, none of the *Bacillus* strains of the composition inhibit the growth of *Bradyrhizobium*, *Rhizobium*, or *Trichoderma* species. Even more preferably, the *Bacillus* strains of the composition secrete anti-fungal metabolites, and the method of this invention does not require cell to cell contact of the *Bacillus* with the pathogen for the suppression of the fungal pathogen activity or growth.

In yet another embodiment, the invention provides a method for inhibiting the growth and/or activity of fungal plant pathogens by applying a composition comprising aerobic or faculatively aerobic, Gram-positive, spore-forming rods of Class Bacilli, Order Bacillales, Family Bacillaceae or Paenibacillaceae, preferably at least three bacterial strains from species of genus *Bacillus*, *Brevibacillus*, and/or *Paenibacillus*, where each strain produces a fungal inhibition zone of at least 1 mm for at least two fungal strains of different genera selected from *Fusarium*, *Phytophthora*, *Pythium*, *Rhizoctonia*, and *Sclerotinia*. In an alternative embodiment, the invention provides a method for inhibiting the growth and/or activity of fungal plant pathogens comprising applying a composition comprising aerobic or faculatively aerobic, Gram-positive, spore-forming rods of Class Bacilli, Order Bacillales, Family Bacillaceae or Paenibacillaceae, preferably three or more bacterial strains from species of genus *Bacillus*, *Brevibacillus*, and/or *Paenibacillus*, where each strain is selected on the basis of at least a 2 mm zone of inhibition against at least two pathogenic fungal genera while maintaining compatibility (<1 mm zone of inhibition) against beneficial soil organisms, optionally *Bradyrhizobium* and/or *Trichoderma*. Typically, the composition comprises at least 1, 2, 3, 4, 5, 6, 7, 8, 9, 10, or 11 *Bacillus* strains. Preferably, the composition comprises at least 2, 3, 4, or 5 *Bacillus* strains. More preferably, composition comprises four *Bacillus* strains. In a preferred mode, at least three bacterial strains are selected from the group consisting of *Brevibacillus laterosporus* strain CM-3, *Brevibacillus laterosporus* strain CM-33, *Bacillus amyloliquefaciens* BCM-CM5 (PTA-121388), *Bacillus licheniformis* ATCC-11946, *Bacillus mojavensis* BCM-01 (PTA-121389), *Bacillus pumilus* NRRL-1875, *Bacillus subtilis* 10 DSM-10, *Bacillus subtilis* NRRL-1650, *Bacillus megaterium* BCM-07 (PTA-121390), *Paenibacillus polymyxa* DSM-36, *Paenibacillus chitinolyticus* DSM-11030, and combinations thereof. In another preferred mode, the at least three bacterial strains are: (a) *Bacillus amyloliquefaciens*, *Bacillus licheniformis*, *Bacillus subtilis* 10, and *Brevibacillus laterosporus* (CM3 and/or CM33); (b) *Bacillus licheniformis*, *Brevibacillus laterosporus* (CM3 and/or CM33), and *Bacillus mojavensis*; (c) *Bacillus amyloliquefaciens*, *Brevibacillus laterosporus* (CM3 and/or CM33), and *Bacillus pumilus* or (d) *Bacillus amyloliquefaciens*, *Brevibacillus laterosporus* (CM3 and/or CM33), *Bacillus pumilus*, and *Paenibacillus polymyxa*. In another embodiment, the composition may comprise BCM-CM5 (PTA-121388), *Bacillus mojavensis* BCM-01 (PTA-121389), *Bacillus megaterium* BCM-07 (PTA-121390), or combinations thereof. Preferably, the composition comprises spores or live cells of bacterial strains. More preferably, the bacteria strains are in spore form. The spores may be formulated in a suspension comprising water, which preferably is substantially chlorine-free. The composition may further comprise nutrient organic compounds, trace minerals, vitamins, growth factors, or adjuvants. Preferably the composition inhibits fungal plant pathogens which are members of the *Fusarium* species, optionally *Fusarium graminearum*, *Fusarium oxysporum*, *Fusarium solani*, *Fusarium verticilliodes*, and/or *Fusarium virguliforme*; *Phytophthora* species, optionally *Phytophthora medicaginis* and/or *Phytophthora sojae*; *Pythium* species, optionally *Pythium aphanidermatum* and/or *Pythium ultimum*, *Rhizoctonia* species, optionally *Rhizoctonia solani*; and/or *Sclerotinia* species, optionally *Sclerotinia sclerotiorum*. More preferably, substantially all of these species of fungal plant pathogens are inhibited. Preferably, the *Bacillus* strains do not inhibit the growth of beneficial rhizosphere microbes. More preferably, the *Bacillus* strains do not inhibit the growth of a *Bradyrhizobium* or *Trichoderma* species. In a preferred mode, the *Bacillus* strains of the composition secrete anti-fungal metabolites. The composition may be applied within 10 days of sowing of the plant seeds, optionally within 3, 5, or 7 days of sowing the seeds. The composition may be applied within 10 days of sowing of the plant seeds, optionally within 1, 2, 3, 4, 5, 6, 7, 8, 9, or 10 days of sowing the seeds. The composition may be applied before the seeds germinate. The composition may be applied to the soil or to the plant foliage after germination, optionally 1, 2, 3, 4, 5, 6, 7, 8, 9, or 10 days after germination.

In still another embodiment, this invention provides a method for selecting a bacterial strain comprising selecting at least three strains from genera of aerobic, spore-formers selected from the group consisting of *Bacillus*, *Brevibacillus*, and *Paenibacillus* and testing whether each of the selected *Bacillus* strains produces a fungal inhibition zone on an agar plate of at least one mm for at least two fungal plant pathogen species selected from the *Fusarium* genus, *Phytophthora* genus, *Pythium* genus, *Rhizoctonia* genus, and *Sclerotinia* genus. Preferably, each plant pathogen fungal species is represented by multiple variant isolates from different geographically located infected field sites and each bacterial strain will exhibit inhibition of multiple variant isolates of the minimum two fungal pathogen species. More preferably, the method further comprises selecting bacteria that have complementary inhibition patterns where the selected bacteria, when combined, collectively inhibit multiple strain variants of all the species of all the plant pathogen fungal genera. Even more preferably, the method further comprises selecting bacteria which do not inhibit the growth of at least one beneficial soil microbe, optionally *Bradyrhizobium* or *Trichoderma*.

BRIEF DESCRIPTION OF THE DRAWINGS

FIG. 3A-K depicts the percent inhibition of plant pathogen species by *Bacillus* strains.

FIG. 12 (A) depicts the percent of pea seeds germinated on Day T=7 (384 seeds per treatment) and (B) depicts the percent of pea seeds germinated on Day T=7 (288 seeds per treatment).

DETAILED DESCRIPTION OF THE INVENTION

Figure 1:
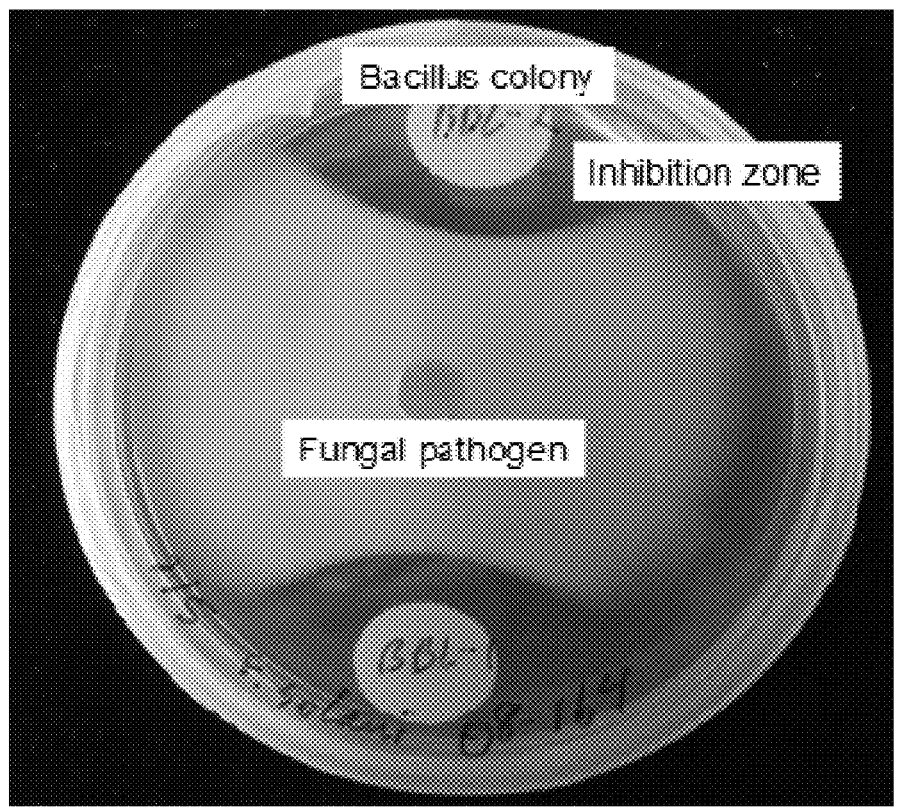
FIG. 1 depicts the "zone of inhibition" measuring method.

The current invention develops and applies a new model for biocontrol in which novel concentrates comprised of specific combinations of *Bacillus* strains are used to suppress the activities and growth of an extremely wide spectrum of fungal plant pathogens while maintaining compatibility with beneficial plant microbes such as *Bradyrhizobium* and *Trichoderma*.

Plant Fungal Pathogens

There are five major fungal genera that cause significant losses across the commercial cash crops. These include:

*Fusarium*:

*Fusarium* is extremely ubiquitous and can survive for long periods in the soil increasing its ability to cause significant crop loss in corn, soy, wheat, and barley. *Fusarium* infects roots and seeds as well as seedlings and can act as a pathogen complex. The species *Fusarium oxysporum* affects a wide variety of hosts of any age. Tomato, tobacco, legumes, cucurbits, sweet potatoes and banana are a few of the most susceptible plants, but it will also infect other herbaceous plants. *Fusarium oxysporum* generally produces symptoms such as wilting, chlorosis, necrosis, premature leaf drop, browning of the vascular system, stunting, and damping-off—the killing of newly emerged or emerging seedlings.

*Pythium*:

*Pythium* also has a large host range including soy and corn. *Pythium* infects and rots seeds and seedlings and can cause the common crop disease root rot. This pathogen can cause both prior and post emergent damage making it a common problem for fields as well as greenhouses.

*Phytophthora*:

*Phytophthora* much like *Pythium* can damage and kill plants throughout the growing season. *Phytophthora* is capable of causing enormous economic losses on crops worldwide. Members of the *Phytophthora* genus are mostly pathogens of dicotyledons, and are relatively host-specific parasites of considerable economic importance. Among the plants that are commonly infected by *Phytophthora* are soybeans, potatoes, strawberries, cucumbers, squash and oak and alder trees.

*Rhizoctonia*:

*Rhizoctonia* is common in many crops and does the most damage to plant seedlings, stunting plant growth leading to significant yield loss. *Rhizoctonia solani* causes a wide range of commercially significant plant diseases. It is one of the fungi responsible for Brown patch (a turf grass disease), damping off in seedlings, as well as black scurf of potatoes, bare patch of cereals, root rot of sugar beet, belly rot of cucumber, sheath blight of rice, and many other pathogenic conditions.

*Sclerotinia*:

*Sclerotinia*—"white mold"—is commonly destructive in the upper Midwest. Lesions develop at stem nodes during or after flowering. *Sclerotinia sclerotiorum* can also be known as cottony rot, watery soft rot, stem rot, drop, crown rot and blossom blight. The host range is over 400 species including major agricultural and horticultural plants; among the most susceptible hosts are soy, snap beans, and sunflowers.

Plant fungal pathogens are typically controlled by the application of chemical fungicides either on the seed, into the soil or by foliar spray. A limited number of commercial biocontrol agents are in use in the current market, but these are single strains of bacteria primarily targeted toward a specific fungal pathogen. The approach thus far for developing biological products to control plant fungal pathogens has been built on and is based on the chemical fungicide model. The standard approach has been and continues to be to isolate and apply a single strain of microbe which exhibits specific activity against a narrow list of target plant specific pathogens.

The present invention applies a new model for biocontrol in which novel concentrates comprising specific combinations of bacterial strains are used to suppress the activities and growth of an extremely wide spectrum of fungal plant pathogens, while maintaining compatibility with beneficial plant microbes such as *Bradyrhizobium* and *Trichoderma*.

The present invention provides compositions comprising mixtures of bacterial strain concentrates selected to inhibit the activities and growth of a broad spectrum of plant pathogens including but not limited to five fungal genera. The compositions of this invention have been successfully tested against thirteen fungal species and fifty-nine distinct fungal pathogen isolates, all of which have been isolated from infected field sites.

For the methods described herein, fungal genera and species representative of both the *Ascomycetes* and *Basidomycetes* were used. See Table 1. From the *Ascomycetes* the *Fusarium* genus (5 species, 23 variant isolates) and the *Sclerotinia* genus (1 species, 4 variant isolates) were used. From the *Basidiomycetes* the *Rhizoctonia* genus (1 species, 15 variant isolates), the *Phytophthora* genus (2 species, 10 variant isolates) and the *Pythium* genus (4 species, 7 variant isolates) were used. These 5 genera comprised of 13 species encompassing 59 different variant isolates is representative of fungal pathogens that infect essentially all plants of commercial importance.

Another characteristic of this invention is that the selected antifungal strains all secrete agar-diffusible anti-fungal metabolites, as demonstrated by a distinct no-growth zone surrounding the *Bacillus* growth colony. No cell to cell contact of the *Bacillus* cells with the pathogen is necessary for the suppression of the fungal pathogen activity or growth.

The bacterial strains described herein may be used to inhibit the growth and/or activity of fungal plant pathogens. For example, the *Bacillus* strain compositions may be used in methods of inhibiting the growth and/or activity of *Fusarium* species, including but not limited to *Fusarium graminearum*, *Fusarium oxysporum*, *Fusarium solani*, *Fusarium verticilliodes*, and *Fusarium virguliforme*; *Phytophthora* species, including but not limited to *Phytophthora medicaginis* and *Phytophthora sojae*; *Pythium* species, including but not limited to *Pythium aphanidermatum* and *Pythium ultimum*, *Rhizoctonia* species, including but not limited to *Rhizoctonia solani*; and *Sclerotinia* species, including but not limited to *Sclerotinia sclerotiorum*.

TABLE 1

Fungal plant pathogen species and number of isolates of each tested.

| Fungal Pathogen species | No. of Isolates tested |
| --- | --- |
| *Fusarium graminearum* | 6 |
| *Fusarium oxysporum* | 5 |
| *Fusarium solani* | 6 |
| *Fusarium verticilliodes* | 1 |
| *Fusarium virguliforme* | 5 |
| *Phytophthora medicaginis* | 9 |
| *Phytophthora sojae* | 1 |
| *Pythium aphanidermatum* | 2 |
| *Pythium ultimum* | 3 |
| *Pythium* undefined species 1 | 1 |
| *Pythium* undefined species 2 | 1 |
| *Rhizoctonia solani* | 15 |
| *Sclerotinia sclerotiorum* | 4 |
| Total pathogen isolates | 59 |

*All fungal pathogen are naturally occurring and were isolated from infected plants/fields.

The bacterial strains of this invention show a high level of inhibition of a broad spectrum of plant pathogens comprising five different fungal genera, thirteen different species and isolates of these fifteen species of pathogenic fungi from fifty-nine different infected field sites. These bacterial strains are combined in complementary ways such that substantially all of the selected virulent plant pathogens are inhibited by the bacterial concentrate. The bacterial strains described herein do not inhibit the growth of beneficial rhizosphere microbes such as *Bradyrhizobium* which is key to symbiotic nitrogen fixation in legumes and *Trichoderma* which is a known endophytic beneficial soil fungus.

Benefits of *Bradyrhizobium* and *Trichoderma* to Soil/Plant Health

*Bradyrhizobium* is a soil bacterium belonging to the larger bacterial group *Rhizobia* which fixes nitrogen inside the root nodules of legumes such soy, peas, and beans. This symbiotic relationship between bacteria and plant is critical because plants cannot readily utilize atmospheric nitrogen and *Rhizobia* cannot fix nitrogen independently of a plant host. Adding further importance to this relationship, *Rhizobia* are the only known nitrogen-fixing bacteria able to establish a symbiotic relationship with legume nodules. Overall, the increased root nodules and useable nitrogen source increase the total plant yield. Because the overuse of nitrogen-containing fertilizers poses a significant environmental threat, the need for nitrogen-fixing *Rhizobium* has become increasingly more important.

Like *Rhizobia*, *Trichoderma* species are plant symbionts whose presence also increase total plant productivity. This increase in plant productivity is due, at least in part, to increased root growth and induced systemic resistance in the presence of *Trichoderma*. Harman, et al. *Nature Reviews Microbiology* 2, 43-56 (January 2004).

*Bacillus* Microbes

Rich, fertile, biologically active soil contains many diverse species of microorganisms which are essential to plant growth and vigor. Among the most common naturally occurring soil microbes are members of the *Bacillus* genus. *Bacillus* are a diverse group of bacteria which can grow aerobically (need air) or facultatively (can grow in presence or absence of air). *Bacillus* are all capable of entering a dormant state by sporulation (forming spores). Dormant spores can be thought of as "bacterial seeds" except that unlike plants, the *Bacillus* becomes the spore not as part of the regular succession of stages in their life cycle but rather in response to stress, which in the soil is most commonly due to nutrient limitation, drought, or temperature extremes.

Compositions according to the present invention contain bacteria which are Gram-positive, aerobic or facultatively aerobic, spore-forming rods. These bacteria will be referred to as, "*Bacillus*," although recent taxonomy has expanded the classification to identify some of the species as belonging to the genera *Brevibacillus* or *Paenibacillus* (See Table 2); however the term "*Bacillus*" as used in this application should be understood to include all three genera. *Bacillus*, which are the subject of the present invention, are added to the soil as soil or seed inoculants. *Bacillus* spores are in essence encapsulated naturally. In addition to having a stable shelf life in product form, the *Bacillus* spores will lie dormant in the soil or on the seed until physical conditions (temperature, moisture, nutrient levels) become favorable to seed germination, at which time the spores will also germinate and grow in the rhizosphere (the soil surrounding the emerging plant roots).

As the plant grows, *Bacillus* vegetative cells, which are progeny of the germinated spores, will grow and propagate in the root zone, exerting their many unique properties in the soil and in interaction with the plant roots. If adverse conditions arise in the soil, such as drought, the *Bacillus* are capable of re-sporulation, followed by re-germination when conditions return to favorable. This ensures that the spore-forming *Bacillus* will have an extended presence in the root zone through the growing season. Non-spore forming soil microbes such as *Actinomyces* and *Pseudomonas* cannot form spores and thus may not survive transient adverse soil conditions. See also U.S. Patent Application Publication No. 2003/004528.

The *Bacillus* of the current invention can be used in combination with other beneficial soil microorganisms, including but not limited to symbiotic nitrogen fixing bacteria of the *Rhizobium* and *Bradyrhizobium* genera, free living beneficial soil bacteria of the *Actinomyces* and *Streptomyces* genera, beneficial filamentous fungi of the *Trichoderma* genus, and *Micorrhizal* fungi of the *Glomus* genus.

The inventors surprisingly found that the use of a suitable mixture of *Bacillus* strains alone could produce anti-fungal activities and increased growth of plants in the absence of any chemical fertilizers.

The *Bacillus* strains that may be used in the compositions and methods described herein include but are not limited to *Brevibacillus laterosporus* strain CM-3 [ATCC Accession No. PTA-3593], *Brevibacillus laterosporus* strain CM-33 [ATCC Accession No. PTA-3592], *Bacillus amyloliquefaciens* BCM-Cm5, *Bacillus licheniformis* ATCC-11946, *Bacillus mojavensis* BCM-01, *Bacillus pumilus* NRRL-1875, *Bacillus subtilis* 10 DSM-10, *Bacillus subtilis* NRRL-1650, *Bacillus megaterium* BCM-07, *Paenibacillus polymyxa* DSM-36, *Paenibacillus chitinolyticus* DSM-11030, and combinations thereof. Alternative designations for these strains are shown in Table 2 herein.

A composition may comprise at least 1, 2, 3, 4, 5, 6, 7, 8, 9, 10, or 11 bacterial strains. A composition may consist of at least 1, 2, 3, 4, 5, 6, 7, 8, 9, 10, or 11 strains. A composition may comprise 2, 3, 4, or 5 strains. A composition may comprise 3 strains. A composition may comprise 4 strains. A composition may comprise strains of at least three different *Bacillus* spp. A composition may comprise strains of two different genera, three different genera, or at least four different *Bacillus* spp.

TABLE 2

*Bacillus* strains screened during fungal plant pathogen study.

| Bacillus | Strain* | Other designations |
|---|---|---|
| Bacillus amyloliquefaciens | BCM-CM5 | BCM strain deposited as PTA-121388 |
| Bacillus licheniformis | ATCC-11946 | (Weigmann) Chester, 1333[B-1001] |
| Bacillus mojavensis | BCM-01 | BCM strain deposited as PTA-121389 |
| Bacillus pumilus | NRRL-1875 | B-1875, C-1479, NRS-2003, 2003 is Smith number; 1479 is NCA number |
| Bacillus subtilis 10 | DSM-10 | ATCC 6051, CCM 2216, IAM 12118, IFO 13719, JCM 1465, LMG 7135, NBRC 13719, NCIB 3610, NCTC 3610, NRS 744 |
| Bacillus subtilis 1650 | NRRL-1650 | B-1650 |
| Bacillus megaterium | BCM-07 | BCM strain deposited as PTA-121390 |
| Brevibacillus laterosporus | BCM-CM3 | BCM strain deposited as ATCC PTA-3593 |
| Brevibacillus laterosporus | BCM-CM33 | BCM strain deposited as ATCC PTA-3592 |
| Paenibacillus polymyxa | DSM-36 | ATCC 842, BUCSAV 162, CCM 1459, JCM 2507, LMG 13294, NCIB 8158, NCTC 10343 |
| Paenibacillus chitinolyticus | DSM-11030 | IFO 15560, NBRC 15660 |

*Strains designated DSM, ATCC, and NRRL are strains obtained from culture collections. Strains designated BCM are naturally occurring *bacillus* strains obtained by BCM (not from culture collections).

*Bacillus* strains designated BCM-CM5, BCM-01, and BCM-07 were deposited on Jul. 15, 2014 with the American Type Culture Collection (ATCC), located at 10801 University Boulevard, Manassas, Va., 20110-2209, USA under terms of the Budapest Treaty, and assigned Accession Numbers PTA-121388, PTA-121389, and PTA-121390, accordingly.

A composition may comprise at least about 1, 2, 3, 4, 5, 6, 7, 8, or $9 \times 10^{10}$ colony forming units per mL (CFU/mL). A colony forming unit (CFU) is an estimation of the total population of viable cells (bacterial or fungal) capable of growing and replicating giving rise to a single colony. This estimation is based upon the assumption a single cell (or spore) gives rise to a single colony—thus a colony forming unit. Because spores will germinate, grow, and replicate on solid media, CFUs can be an estimate of viable cell or spores. CFUs in the total population may be estimated by serially diluting the given culture or solution and evenly spreading a single dilution on a solid complex medium such as Tryptic Soy Agar (TSA) and incubating at 37° C. overnight. The number of colonies which grow overnight multiplied by the total dilution factor will give the number of CFUs/mL, an estimate of the number of viable spores and/or cells/mL. Spore estimates may be done in the same protocol with the added step of holding the dilution at 80° C. for 5 minutes before spreading on solid media; this step ensures all vegetative cells are killed. Spores, which are able to withstand high heat, remain unharmed during this 80° C. incubation. Where a composition comprises more than one *Bacillus* strain, the same protocol may be used, and the concentration of individual strains may be determined from their distinct and differentiable colony morphology.

The CFU/ml of each *Bacillus* strain in the formulated *Bacillus* strain concentrates can vary from $1 \times 10^3$ CFU/ml up to $1 \times 10^{12}$ CFU/ml. The dose of each *Bacillus* strain in the *Bacillus* strain concentrates, when applied to soil or seed, should be such that the concentration in the Rhizosphere (root zone) near the seed is a minimum per *Bacillus* strain of $1 \times 10^3$ CFU/gram of soil with a range of $1 \times 10^3$ CFU/gram soil up to $1 \times 10^{11}$/gram soil. For seed coating applications the minimum dose of each *Bacillus* strain in the *Bacillus* strain concentrates should be a minimum of $1 \times 10^3$ CFU/seed with a range of $1 \times 10^3$ CFU/seed up to $1 \times 10^{10}$ CFU/seed. The total number of CFU in the product, in the Rhizosphere, and/or on the seed will be the sum of the CFU for each strain present.

A liquid composition may comprise at least about 1, 2, 3, 4, 5, 6, 7, 8, or $9 \times 10^{12}$ colony forming units per mL (CFU/mL). A liquid composition may comprise at least about 1, 2, 3, 4, 5, 6, 7, 8, or $9 \times 10^{11}$ colony forming units per mL (CFU/mL). A liquid composition may comprise at least about 1, 2, 3, 4, 5, 6, 7, 8, or $9 \times 10^{10}$ colony forming units per mL (CFU/mL). A liquid composition may comprise at least about 1, 2, 3, 4, 5, 6, 7, 8, or $9 \times 10^9$ colony forming units per mL (CFU/mL). A liquid composition may comprise at least about 1, 2, 3, 4, 5, 6, 7, 8, or $9 \times 10^8$ colony forming units per mL (CFU/mL). A liquid composition may comprise at least about 1, 2, 3, 4, 5, 6, 7, 8, or $9 \times 10^7$ colony forming units per mL (CFU/mL). A liquid composition may comprise at least about 1, 2, 3, 4, 5, 6, 7, 8, or $9 \times 10^6$ colony forming units per mL (CFU/mL). A liquid composition may comprise at least about 1, 2, 3, 4, 5, 6, 7, 8, or $9 \times 10^5$ colony forming units per mL (CFU/mL). A liquid composition may comprise at least about 1, 2, 3, 4, 5, 6, 7, 8, or $9 \times 10^4$ colony forming units per mL (CFU/mL). A liquid composition may comprise at least about 1, 2, 3, 4, 5, 6, 7, 8, or $9 \times 10^3$ colony forming units per mL (CFU/mL). Preferred ranges of CFU concentration according to this invention may be the range between any two concentration levels identified in this paragraph.

Particularly preferred ranges for liquid composition may comprise between at least about $0.1\text{-}1 \times 10^9$ colony forming units per mL (CFU/mL). A liquid composition may comprise between at least about $10^6\text{-}10^{10}$ colony forming units per mL (CFU/mL). A liquid composition may comprise between at least about $1 \times 10^7\text{-}1 \times 10^9$ colony forming units per mL (CFU/mL). A liquid composition may comprise between at least about $1 \times 10^8\text{-}1 \times 10^9$ colony forming units per mL (CFU/mL). A liquid composition may comprise between at least about $1 \times 10^6\text{-}1 \times 10^8$ colony forming units per mL (CFU/mL). A liquid composition may comprise between at least about $1 \times 10^7\text{-}1 \times 10^8$ colony forming units per mL (CFU/mL). A liquid composition may comprise between at least about $1 \times 10^8\text{-}1 \times 10^{10}$ colony forming units per mL (CFU/mL). A liquid composition may comprise between at least about $1 \times 10^3\text{-}1 \times 10^6$ colony forming units per mL (CFU/mL). A liquid composition may comprise between at least about $1 \times 10^4\text{-}1 \times 10^{11}$ colony forming units per mL (CFU/mL). A liquid composition may comprise between at least about $1 \times 10^5\text{-}1 \times 10^{12}$ colony forming units per mL (CFU/mL). A liquid composition may comprise between at least about $1 \times 10^3\text{-}1 \times 10^{12}$ colony forming units per mL (CFU/mL).

A dried powder composition may comprise at least about 1, 2, 3, 4, 5, 6, 7, 8, or $9 \times 10^{12}$ colony forming units per gram (CFU/gram). A dried powder composition may comprise at least about 1, 2, 3, 4, 5, 6, 7, 8, or $9 \times 10^{11}$ colony forming units per gram (CFU/gram). A dried powder composition may comprise at least about 1, 2, 3, 4, 5, 6, 7, 8, or $9 \times 10^{10}$ colony forming units per gram (CFU/gram). A dried powder composition may comprise at least about 1, 2, 3, 4, 5, 6, 7, 8, or $9\times10^9$ colony forming units per gram (CFU/gram). A dried powder composition may comprise at least about 1, 2, 3, 4, 5, 6, 7, 8, or $9\times10^8$ colony forming units per gram (CFU/gram). A dried powder composition may comprise at least about 1, 2, 3, 4, 5, 6, 7, 8, or $9\times10^7$ colony forming units per gram (CFU/gram). A dried powder composition may comprise at least about 1, 2, 3, 4, 5, 6, 7, 8, or $9\times10^6$ colony forming units per gram (CFU/gram). A dried powder composition may comprise at least about 1, 2, 3, 4, 5, 6, 7, 8, or $9\times10^5$ colony forming units per gram (CFU/gram). A dried powder composition may comprise at least about 1, 2, 3, 4, 5, 6, 7, 8, or $9\times10^4$ colony forming units per gram (CFU/gram). A dried powder composition may comprise at least about 1, 2, 3, 4, 5, 6, 7, 8, or $9\times10^3$ colony forming units per gram (CFU/gram). Preferred ranges of CFU concentration according to this invention may be formed between any two concentration levels identified in this paragraph.

Particularly preferred ranges for a dried powder composition may comprise between at least about $0.1\text{-}1\times10^9$ colony forming units per gram (CFU/gram). A dried powder composition may comprise between at least about $1\times10^6\text{-}1\times10^9$ colony forming units per gram (CFU/gram). A lyophilized composition may comprise between at least about $1\times10^6\text{-}1\times10^9$ colony forming units per gram (CFU/gram). A dried powder composition may comprise between at least about $1\times10^7\text{-}1\times10^9$ colony forming units per gram (CFU/gram). A dried powder composition may comprise between at least about $1\times10^8\text{-}1\times10^9$ colony forming units per gram (CFU/gram). A dried powder composition may comprise between at least about $1\times10^6\text{-}1\times10^{10}$ colony forming units per gram (CFU/gram). A dried powder composition may comprise between at least about $1\times10^6\text{-}1\times10^8$ colony forming units per gram (CFU/gram). A dried powder composition may comprise between at least about $1\times10^7\text{-}1\times10^8$ colony forming units per gram (CFU/gram). A dried powder composition may comprise between at least about $1\times10^8\text{-}1\times10^{10}$ colony forming units per gram (CFU/gram). A dried powder composition may comprise between at least about $1\times10^3\text{-}1\times10^6$ colony forming units per gram (CFU/gram). A dried powder composition may comprise between at least about $1\times10^4\text{-}1\times10^{11}$ colony forming units per gram (CFU/gram). A dried powder composition may comprise between at least about $1\times10^5\text{-}1\times10^{12}$ colony forming units per gram (CFU/gram). A dried powder composition may comprise between at least about $1\times10^3\text{-}1\times10^{12}$ colony forming units per gram (CFU/gram).

The CFU/ml or gm of the formulated *Bacillus* strain concentrates can vary from $1\times10^3$ CFU/ml or /gm up to $1\times10^{12}$ CFU/ml or /gm. The dose of the *Bacillus* strain concentrates when applied to soil or seed should be such that the concentration in the Rhizosphere (root zone) near the seed is a minimum per *Bacillus* strain of $1\times10^3$ CFU/gm of soil with a range of $1\times10^3$ CFU/gm soil up to $1\times10^{11}$/gm soil.

For seed coating applications the minimum dose of the *Bacillus* strain concentrates should be a minimum of $1\times10^3$ CFU/seed with a range of $1\times10^3$ CFU/seed up to $1\times10^{10}$ CFU/seed.

Preparing a Spore Suspension

The CFUs in the compositions of this invention are obtainable by growing cells of the respective *Bacillus* strains in liquid monoculture using well-known techniques for bacterial culture. The cells are grown to high density to induce sporulation. Suitable microbiological media for the cultivation of *Bacillus* strain spores include Tryptic Soy Broth (TSB) and Schaeffer's Sporulation Medium, as discussed in *Biology of Bacilli* (Doi, et al. Butterworth-Heinemann, 1992). In one embodiment, the medium of choice is prepared in baffled Erlenmeyer flasks and sterilized at 121° C. under 15 psig for 30 minutes, or until rendered sterile. One may under fill the Erlenmeyer flasks to optimize aeration during shaking; 200 ml of medium works well in a 4 liter Erlenmeyer flask. The flask may be fitted with a sterile filter cap that allows the contents to breadth without becoming contaminated. The sterile medium is inoculated from a slant culture on tryptic soy agar, preferably by having a slant medium with good colony growth melted and poured into the Erlenmeyer flask. The inoculated medium is then shaken on a rotary orbital shaker at 100-200 rpm and incubated at 32° C. for 48 hours. Thus prepared, the *Bacillus* strains may be 90% sporulated by 48 hours. If vegetative cells are required, a sample thereof can be taken from the suspension at 18-24 hours after inoculation. Typically, when using TSB as the medium, a viable spore count of about $10^8$/mL will be reached within 48 hours.

The resulting spore suspension, without further preparation, can be applied to rice or other grain plants. If the spore suspension is not used within one week of preparation, it may be refrigerated at 5° C. to preserve it for later use, such spore suspensions refrigerated at 5° C. have a half-life of about two months when prepared according the above procedure. The spores may be isolated by spray drying. The dried spores may be stored at room temperature (e.g., about 25° C.).

Protocol for Generation of Spores

In an alternative embodiment, suitable microbiological media for the cultivation of *Bacillus* spores include complex media supplemented with glucose (carbon source) and glutamate (nitrogen source). In one embodiment, the medium of choice is prepared in baffled Erlenmeyer flasks and sterilized at about 121° C. under 15 psig for 30 minutes, or until rendered sterile. One may under fill the Erlenmeyer flasks to optimize aeration during shaking; 1 liter of medium in a 3 liter baffled Erlenmeyer flask works well. The flask may be fitted with a sterile sponge cap that allows the contents to breathe without becoming contaminated. The sterile medium is inoculated with a single, well isolated, typical colony from Tryptic Soy Agar (TSA), a complex solid medium well suited for the propagation of a wide variety of bacteria and fungi. The inoculated medium is then shaken on a rotary orbital shaker at about 190-250 rpm and incubated at 37° C. for about 24 to 48 hours. Thus prepared, the *Bacillus* strains may be about 85-95% sporulated by 24 to 48 hours. These spores may be recovered by centrifugation or more commonly used as a "seed." This "seed" may be used to inoculate large scale production fermentation vessels filled with similar media. The culture may be fermented under typical conditions used for growing aerobic bacteria: incubate at 35-38° C. with an air sparge rate of 0.75-1.50 VVM (volume of air/volume of liquid/minute), and constant agitation via an impeller. The culture is fermented until the desired spore population is reached. The spore population will increase as the cells are starved for a carbon source such as glucose but the final population of spores attained is somewhat strain specific. For the present invention the culture is grown to a final spore concentration $1\times10^9$ to $1\times10^{10}$ CFU/mL.

The above spore suspension may be stabilized by dropping the pH to 4.2-4.5 by adding acid and then concentrated by centrifugation. The concentrated slurry may be spray-dried at which point the spores are stable for at least 12 months at room temperature. Because spores will germinate when proper conditions (temperature, nutrients) exist—in the soil, for example—they can be applied to crops directly or mixed with a nutrient solution to facilitate germination and then applied. The freshly mixed spore suspension should be mixed thoroughly before application and should ideally be used within 48 hours.

For quality assurance, all products, dry and liquid, are assayed for viable total population using CFU/mL.

The *Bacillus* strain spores may also be purified or concentrated using methods such as ultra-filtration, centrifugation, spray-drying or freeze-drying to generate a packaged product.

Formulations

The composition may be formulated to allow for storage, transport, and/or application to soil and/or crops. The formulation of mixtures of the strains may be adjusted to optimize stability and sporulation. CFUs as spores and/or viable cells should be presented at the concentrations described herein.

The spores may be present in a composition that includes water, or water and additives and excipients that do not have a deleterious effect on the action of the spores, or water, additives and excipients and other ingredients conventionally used in spore preparations, e.g., binders, dry feeds, and the like. The composition may also include certain nutrient organic compounds and trace minerals or vitamins, or growth factors and adjuvants, although it is unknown if all of these additives act to increase crop yield. Vitamin additives may be selected, for example, from pantothenic acid, pyridoxine, riboflavin, thiamin, 25-hydroxy vitamin A, and vitamins B12, C, D, E, K, biotin, choline, folacin and niacin. Mineral additives may be selected, for example, magnesium, potassium, sodium, copper, iodine, iron, manganese calcium, phosphorous, selenium, chlorine and chromium pincolinate. The concentration of the vitamins and minerals will depend upon the plant being treated but, in general, will be between about 0.01% and about 5% by weight of the dry matter.

The *Bacillus* strains may also be combined with other bacterial species, including but not limited to Shroth's gram-negative *Pseudomonas* species. This *Pseudomonas* species has been described as being effective in producing siderophores, which compounds are believed to be the mode-of-action for a demonstrated increase in crop production by application of this *Pseudomonas* species. However, since there are strains of *Pseudomonas* species that are plant pathogens, and since plasmid transfer within a bacterial species can be commonplace, there is a concern such transfer could convert a previously harmless strain into a pathogenic strain.

Applying *Bacillus* Strains to Crops

The *Bacillus* strain concentrates of this invention can be applied to the soil, to the seed or as a foliar application in a variety of forms including liquids and solids of various formulations, such as those described herein. The CFU/ml or gm of the formulated *Bacillus* strain concentrates can vary from $1 \times 10^3$ CFU/ml or /gm up to $1 \times 10^{12}$ CFU/ml or /gm. The dose of the *Bacillus* strain concentrates when applied to soil or seed should be such that the concentration in the Rhizosphere (root zone) near the seed is a minimum per *Bacillus* strain of $1 \times 10^3$ CFU/gm of soil with a range of $1 \times 10^3$ CFU/gm soil up to $1 \times 10^{11}$/gm soil. For seed coating applications the minimum dose of the *Bacillus* strain concentrates should be a minimum of $1 \times 10^3$ CFU/seed with a range of $1 \times 10^3$ CFU/seed up to $1 \times 10^{10}$ CFU/seed.

The spores can be applied as an aqueous suspension obtained directly from the fermentation process described above, or, if the spores are purified or concentrated using methods such as ultra-filtration, centrifugation, spray-drying or freeze-drying, they should be re-suspended in water before application to crops. When the spores are applied as an aqueous suspension taken directly from the fermentation broth, other substances present in the broth will also be applied to the crops. These non-viable substances, such as bacterial metabolites or un-utilized microbial nutrients, will be applied to the plants in very small concentrations, such as 100 grams/ha or less. This level of non-viable substance will not deleteriously affect the crop.

*Bacillus* strains as described herein may be applied to any type of grain, and to both conventional and hybrid varieties. During grow-out, applications of the spore suspension can be made manually, by backpack sprayer or by a more sophisticated mode such as by helicopter spraying or by any mechanical spraying device known for use in farming practice.

The *Bacillus* strains spores can be applied to crops by direct application to the soil, coating of the seeds prior to planting, spraying on the soil, spraying on crops after the seeds germinate, or within 2 weeks of the seedlings emerging. The composition may be applied to the soil, to the plant foliage, to the plant seeds, during sowing of said plant seeds, or after said plants germinate. The composition may be applied after a period of rain or watering of said plants. The composition may be applied within 10 days of sowing of the plant seeds, optionally within 3, 5, or 7 days of sowing the seeds. The composition may be applied before germination, optionally within 1, 2, 3, 4, 5, 6, 7, 8, 9, or 10 days of sowing the seeds. The composition may be applied after germination, optionally 1, 2, 3, 4, 5, 6, 7, 8, 9, or 10 days after germination. The composition may be applied by spraying plants or mixing into soil. The composition may be applied to the root zone. The composition may be around the seed of the plant. The composition may preferably be applied to a plant or soil when the air temperature is over 65° F. The composition may be admixed with a soil. The composition/soil mixture may be applied to the plants, seeds, or seedlings. The composition may be applied at any temperature appropriate for field work, because if the temperature is not suitable for germination, then the spores will lie dormant until an adequate temperature occurs. The composition may be applied within 2 weeks of plant emergence. The plants may be dipped into a liquid spore composition, optionally comprising about $250 \times 10^6$ to $5 \times 10^9$ CFU/mL of the *Bacillus* strains described herein. The plants may be dipped for about 1-30 seconds or 30 seconds and then planted. The plants may be treated a second time, by spraying the plants about 14 days after treatment by dipping.

The composition may be sprayed directly onto row crops as a foliar spray. The crops may be a grain crop, optionally rice, corn, alfalfa, oats, wheat, barley, or hops. The crop may be wheat, soybeans, cabbage, ornamental flowers, optionally geraniums, petunias, daffodils, or trees, optionally poplar trees. New seedling fruit trees or bushes may be dipped into containers comprising a liquid spore concentrate. Crops whose treatment is contemplated and suitable application routes, are shown in Table 3

The crops may be treated with a composition comprising a *Bacillus* strain bacteria selected from the group consisting of *Brevibacillus laterosporus* strain CM-3, *Brevibacillus laterosporus* strain CM-33, *Bacillus amyloliquefaciens* BCM-CM5, *Bacillus licheniformis* ATCC-11946, *Bacillus mojavensis* BCM-01, *Bacillus pumilus* NRRL-1875, *Bacillus subtilis* 10 DSM-10, *Bacillus subtilis* NRRL-1650, *Bacillus megaterium* BCM-07, *Paenibacillus polymyxa*

DSM-36, *Paenibacillus chitinolyticus* DSM-11030, and combinations thereof. The composition may comprise at least 1, 2, 3, 4, 5, 6, 7, 8, 9, 10, or 11 of said strains. The composition may comprise at least 2, 3, 4, or 5 of said strains. The composition may comprise spores or live cells of *Bacillus* strains. The *Bacillus* strain bacteria may be in spore form. The spores may be formulated in a suspension comprising water including but not limited to substantially chlorine-free. The composition may further comprise nutrient organic compounds, trace minerals, vitamins, growth factors, or adjuvants. The *Bacillus* strain bacteria may be applied to the crops in a concentration of $1 \times 10^3$ to $1 \times 10^{12}$ cells/mL or $1 \times 10^3$ to $1 \times 10^{12}$ cells/gram of soil. The composition may be spray-dried or lyophilized. The spores may be obtained by ultra-filtration, centrifugation, spray-drying, freeze-drying, or combinations thereof. The spores will preferably germinate and colonize the soil.

The application of the *Bacillus* composition may inhibit the growth and/or activity of fungal plant pathogens, optionally a member of the *Fusarium* species, optionally *Fusarium graminearum, Fusarium oxysporum, Fusarium solani, Fusarium verticilliodes*, and *Fusarium virguliforme; Phytophthora* species, optionally *Phytophthora medicaginis* and *Phytophthora sojae; Pythium* species, optionally *Pythium aphanidermatum* and *Pythium ultimum, Rhizoctonia* species, optionally *Rhizoctonia solani*; and *Sclerotinia* species, optionally *Sclerotinia sclerotiorum*. The composition may be applied after a fungal pathogen is present.

TABLE 3

Crops and Exemplary Applications Routes

| CROP | IN FURROW APPLICATION | SEED TREATMENT | SEEDLING ROOT DIP | FOLIAR-YOUNG PLANT | FOLIAR MATURE |
|---|---|---|---|---|---|
| Soybeans and other legumes including peanuts | X | X | | X | X |
| Corn, maize | X | X | | X | |
| Wheat, rye, barley and other grasses | X | X | | X | |
| Ornamental flowers | | | X | X | X |
| Fruit trees (apple, peaches, pears, plums etc) | X | | X | X | X |
| Fruit bushes (grapes, raspberries, blueberries, strawberries, blackberries etc) | | | X | X | X |
| Vegetables (tomatoes, all beans, peas, broccoli, cauliflower) | X | | X | X | |
| Root vegetables (potatoes, carrots, beets) | X | | X | X | |
| Decorative trees such as poplar | X | | X | | |
| Vine vegetables such as cucumbers, pumpkins, zucchini | X | | | X | X |

All publications (e.g., Non-Patent Literature), patents, patent application publications, and patent applications mentioned in this specification are indicative of the level of skill of those skilled in the art to which this invention pertains. All such publications (e.g., Non-Patent Literature), patents, patent application publications, and patent applications are herein incorporated by reference to the same extent as if each individual publication, patent, patent application publication, or patent application was specifically and individually indicated to be incorporated by reference.

Although methods and materials similar or equivalent to those described herein may be used in the invention or testing of the present invention, suitable methods and materials are described herein. The materials, methods and examples are illustrative only, and are not intended to be limiting.

The invention now being generally described, it will be more readily understood by reference to the following examples, which are included merely for purposes of illustration of certain aspects and embodiments of the present invention, and are not intended to limit the invention.

EXAMPLES

Example 1

Screening for Fungal Inhibition

A standard agar-plate-based zone-of-inhibition method was used to screen select members of the *Bacillus, Brevibacillus*, or *Paenibacillus* genera comprising 9 different species and a total of 11 different strains. The 11 strains of *Bacillus, Brevibacillus*, or *Paenibacillus* and their identity are given in Table 2. The 13 species of fungal plant pathogens tested are listed in Table 1.

The zone-of-inhibition screening methodology is given in FIG. 1. Fungal pathogen species were grown on Potato Dextrose Agar (PDA) except for *Phytophthora* which was grown on V8 Agar. All fungi were stored at 4° C. until used. *Bacillus* strains were subcultured in LB broth overnight at 37° C. with shaking at 200 rpm. The subculture (0.5 ml) was used to inoculate 50 ml LB broth and grown overnight at 37° C. with shaking at 200 rpm. An 8 mm plug from the center of an agar plate (TSA, 6.5 pH) was removed. An 8 mm plug of pathogen was placed in the empty hole. 10 µl of the *Bacillus* strain was added at appropriate time to the perimeter of the plate (up to 3 *Bacillus* strains per plate). Plates were incubated at room temperature until the pathogen covered the plate. Pathogen inhibition zones were measured with calipers at 90° angle as shown in FIG. 1. The mean of two zone measurements were reported and scored only measured if they were 1 mm or greater. Experiments were performed in duplicate.

Figure 2K:
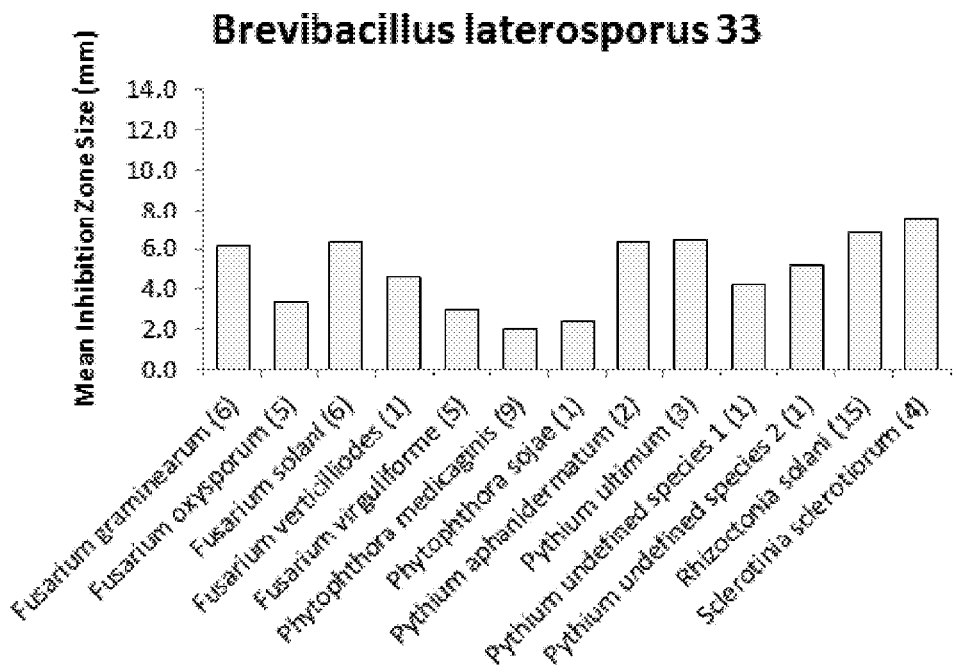
FIG. 2 A-K depicts the mean inhibition zone sizes of plant pathogen species by *Bacillus* strains.

The mean inhibition zone sizes (in mm) of plant pathogens when grown in the presence of *Bacillus* strains are shown graphically in FIG. 2. Each *Bacillus* strain shows a distinct profile in ability to inhibit fungal plant pathogens. While species such as *Bacillus subtilis* inhibits at least one member of every fungal genera, others such as *Bacillus megaterium* and *Paenibacillus chitinolyticus* only inhibit one or two fungal genera.

Figure 3K:
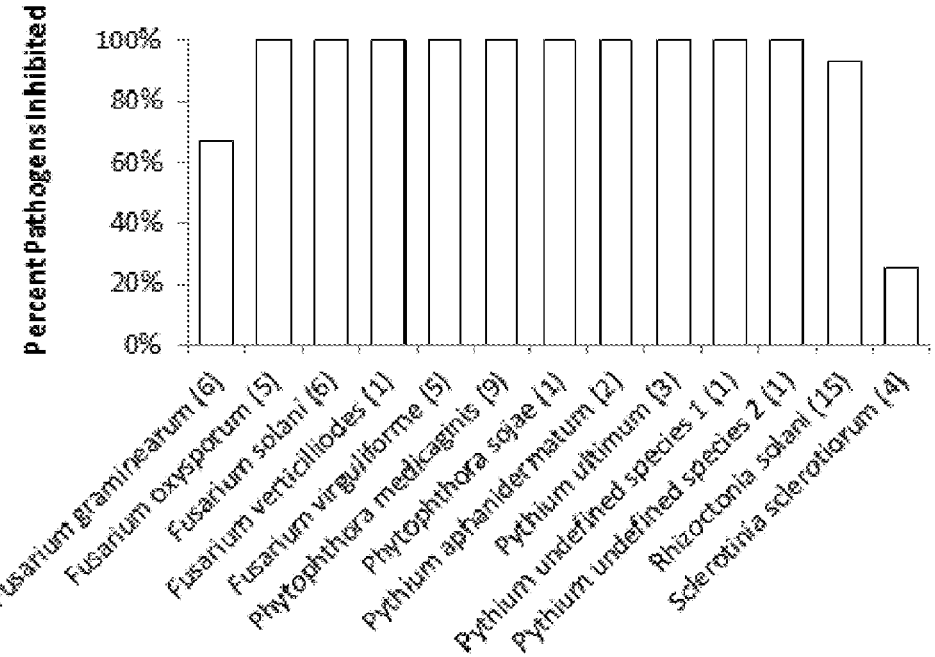

The percent of plant pathogen species inhibited when grown in the presence of *Bacillus* strains are shown graphically in FIG. 3. Each *Bacillus* strain shows a distinct profile in ability to inhibit fungal plant pathogens. While species such as *Bacillus subtilis* inhibit nearly all 59 pathogen isolates, others such as *Bacillus megaterium* and *Paenibacillus chitinolyticus* only inhibit a couple of isolates.

Figure 4:
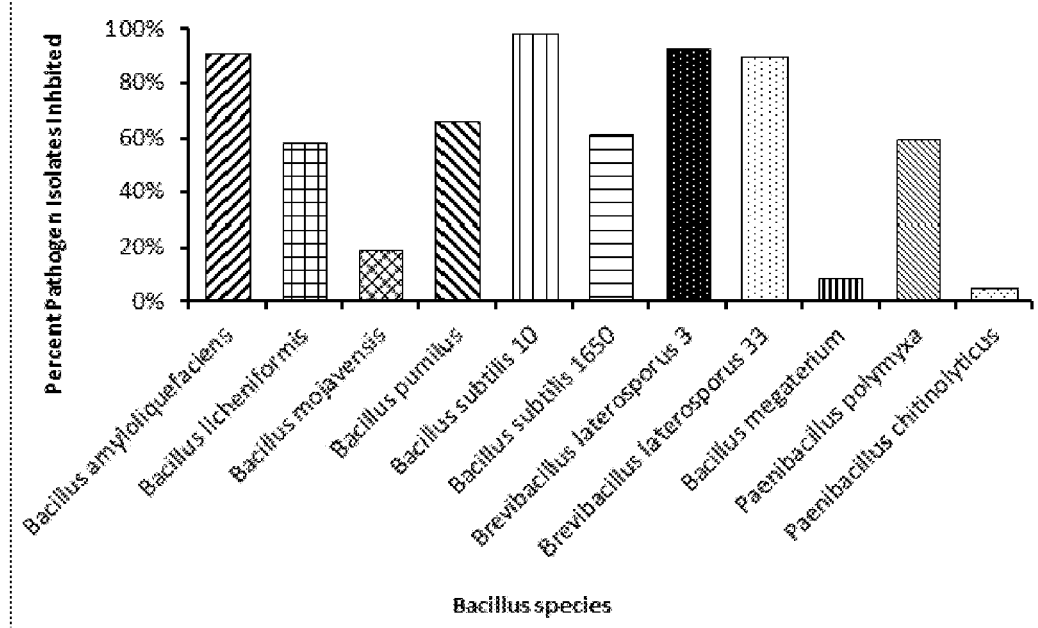
FIG. 4 depicts the percent fungal pathogens inhibited by *Bacillus* strains.

FIG. 4 highlights the percent of fungal plant pathogen isolates inhibited by each *Bacillus* strain. The combination of all data figures leads to the following novel combination of *Bacillus* strain concentrates to control fungal plant pathogen activity and growth:

1: *Bacillus amyloliquefaciens, Bacillus licheniformis, Bacillus subtilis* 10, and *Brevibacillus laterosporus* (CM3 and/or CM 33)

2: *Bacillus licheniformis, Brevibacillus laterosporus* (CM3 and/or CM 33), and *Bacillus mojavensis*

3: *Bacillus amyloliquefaciens, Brevibacillus laterosporus* (CM3 and/or CM 33), and *Bacillus pumilus*

4: *Bacillus amyloliquefaciens, Brevibacillus laterosporus* (CM3 and/or CM 33), *Bacillus pumilus* and *Paenibacillus polymxa*

The initial screen for *bacillus* antifungal properties were completed on solid agar media (TSA). Because there was no actual contact between the *Bacillus* and the fungus, the zone of inhibition of fungal growth observed in the presence of *Bacillus* had to be due to an agar diffusible compound produced and excreted by the *Bacillus*.

This test may be used to evaluate the antifungal activity of the compositions and methods described herein. Combinations of strains/species may be selected based on their efficacy against pathogens in vitro as shown in this test. This test allows for the selection of combinations of *Bacillus* to target multiple fungal pathogens. For example, a combination may be selected to combine different *Bacillus* species/strains that have antifungal activity to target a larger group of pathogens together than the *Bacillus* species/strains would individually. The inventors surprisingly discovered that combinations of *Bacillus* strains/species described herein shown unexpected improved antifungal properties as compared to single strains (or species).

Example 2

Compatibility of *Bacillus* Concentrates with *Bradyrhizobium* and *Trichoderma*

Selected *Bacillus* concentrates and individual *Bacillus* cultures were tested for inhibition of two beneficial soil microbes *Bradyrhizobium*, a naturally occurring bacteria of critical importance in legume symbiotic nitrogen fixation, and *Trichoderma*, a naturally occurring beneficial soil fungus. Commercially available soil inoculant products were used as sources for the two microbes.

For *Bradyrhizobium* a cross streak assay was used in which a center streak of *Bradyrhizobium* was made and then cross streaks of the *Bacillus* cultures to be tested were streaked perpendicular to and just touching the center *Bradyrhizobium* streak. *Bacillus* cross streaks were done at 0, 2, 4 and 6 days after the initial *Bradyrhizobium* streak and the plates were incubated until good growth was obtained for both *Bradyrhizobium* and *Bacillus*.

Figure 5A:
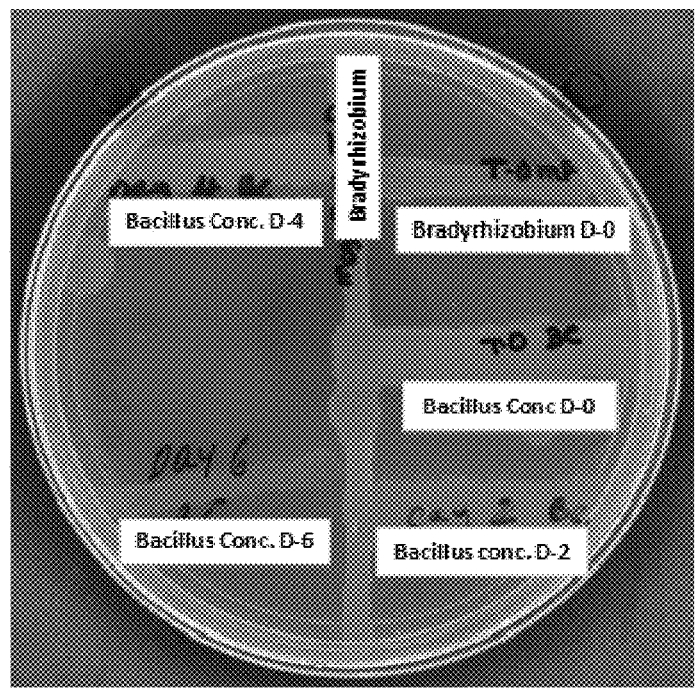
FIG. 5 shows that the *Bacillus* concentrate does not inhibit the growth of beneficial *Bradyrhizobium* and depicts the *Bacillus* and *Bradyrhizobium* compatibility.
Figure 5B:
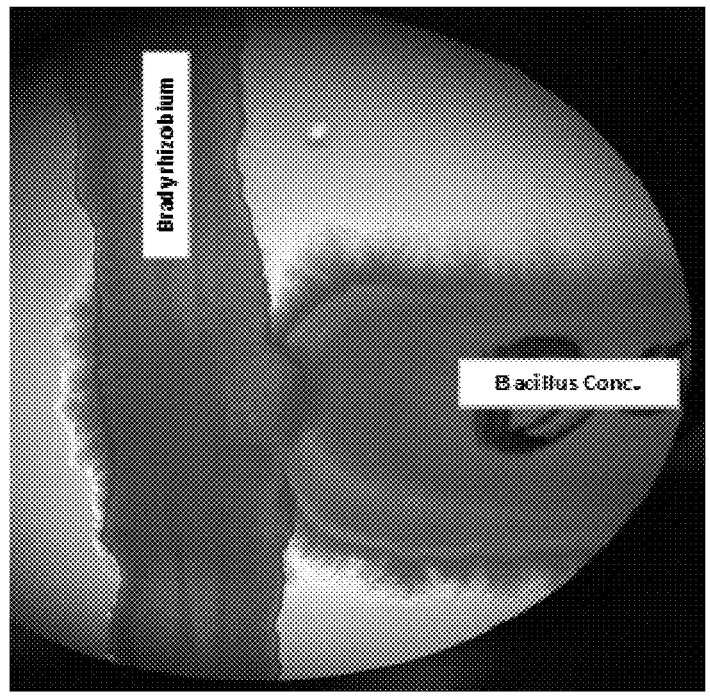

From FIG. 5 it is clear that there is no inhibition of growth of *Bradyrhizobium* by the *Bacillus* cultures.

Figure 6A:
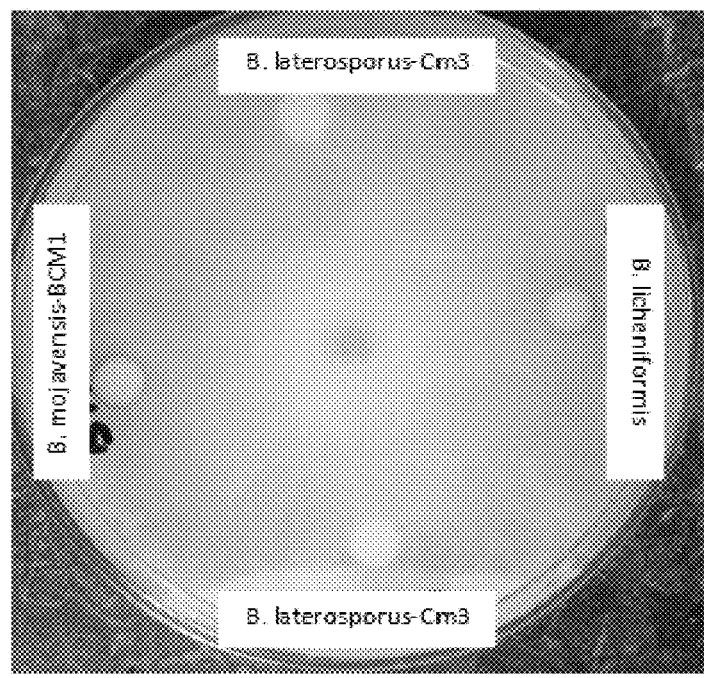
FIG. 6A-B depicts the *Bacillus* and *Trichoderma* compatibility.
Figure 6B:
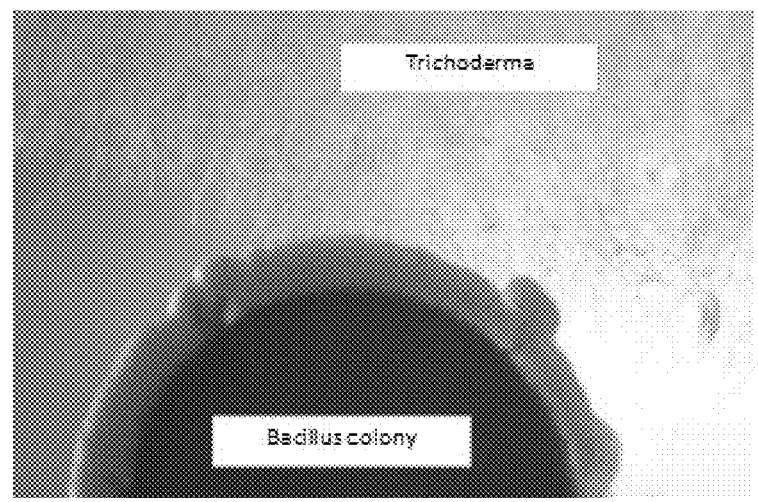

Experiments were conducted by placing discs containing equal amount of each cultures (0.05 ml) on agar plates as shown in FIG. 6. The *Trichoderma* was added to the middle of each Tryptic Soy Agar (TSA) plate. The plate was the incubated at 37° C. for, and monitored every 12-18 hours until fungus covered the entire plate. Additionally, another plate was incubated at 37° C. for 3 days with the *Bacillus* strains alone. The *Trichoderma* was then added to the middle of those plates and incubated again at 37° C. In neither case was there inhibition of the *Trichoderma* by *Bacillus*.

From FIGS. 5 and 6 it is clear that these *Bacillus* strains do not inhibit either *Bradyrhizobium* or *Trichoderma*.

Example 3

Field Study

In vitro results may be further confirmed by in vivo greenhouse and/or field trials. During the greenhouse trials each set of 6 plants will be infected with a representative *Fusarium, Phytophthora, Pythium, Rhizoctonia*, or *Sclerotinia* in the presence and absence *Bacillus* strain concentrate. Total plant growth, root mass, and fungal population will be assessed for all sets of plants.

Example 4

Greenhouse Study

In vitro results of Examples 1 and 2 were confirmed by in vivo greenhouse trials. Planting medium starter bricks were rehydrated with water at T=−5 days. On T=−3 days the hydrated planting medium was inoculated by direct mixing into the hydrated planting medium starter bricks with freshly prepared fungal inoculum (either a mix of 3 *Pythium ultimum* isolates or a mix of 3 *Rhizoctonia solani* isolates), fungal pathogen and *Bacillus* Blend 1 (*Brevibacillus laterosporus* 3 and 33, *Bacillus licheniformis*, and *Bacillus mojavensis*) or *Bacillus* Blend 2 (*Brevibacillus laterosporus* 3 and 33, *Bacillus licheniformis, Bacillus subtilis* 10, and *Bacillus amyloliquefaciens*), or equivalent volume of water as the control.

On planting day (T=0) inoculated soil medium was separately distributed into several 24 well starter flats beginning with the control. Four pea seeds were planted into each well at the depth of ½ inch and starter trays were placed onto an indoor growth light table with enclosing cover and checked daily for germination. Temperature was maintained at a constant 31° C. Germination counts were recorded on day 7 post planting (T=+7 days) and the experiment terminated at T=+14 days.

Observations for growth were recorded at T=7 days. In both test cases, *Pythium* and *Rhizoctonia* caused damping off, observed as low germination and stunted growth. Both *Bacillus* Blend 1 and *Bacillus* Blend 2 were able to suppress the effects of the fungal pathogen observed as higher germination numbers (FIGS. 12A and 12B) and larger, healthier plants (FIG. 1). Observations at T=14 days showed no increase of disease or seedling die-off other than that observed at T=7 days.

From this data it is clear that the mixtures of *Bacillus* inhibit the growth and activity of *Pythium* and *Rhizoctonia* plant pathogens, leading to higher germination and larger, healthier plants. Accordingly, mixtures of *Bacillus* cells as described herein, including but not limited to the mixtures described in this Example, as well as Examples 1 and 2, may be expected to lead to higher germination and larger, healthier plants as described herein.

Example 5

Formulation of a Liquid Concentrate of Six *Bacillus* Strains

Spores from six (6) strains of *Bacillus* are grown in monoculture as described herein, and the liquid concentrates from the respective centrifugation steps are stabilized as described herein. An amount from each of the six *Bacillus* strain liquid concentrates is mixed into a diluting liquid with a standard multiple blade, flat blade impeller at a sufficient RPM such that the desired final concentration of each *Bacillus* strain was attained. The equipment for liquid mixing and blending can be any liquid mixing equipment standard and known to one skilled in the art of liquid formulation. Sufficient power per volume must be used to ensure good hydration of all solid components and good mixing to attain a homogeneous blend. The final concentration of each of the *Bacillus* strains can range from $1 \times 10^3$ CFU/ml final liquid up to $1 \times 10^{11}$ CFU/ml final liquid but is more generally in the range of $1 \times 10^8$ CFU/ml of final liquid up to $1 \times 10^{10}$ CFU/ml of final liquid.

The composition of the diluting liquid can be water, or water, additives and excipients that do not have a deleterious effect on the action of the spores or water, additives and excipients and other ingredients conventionally used in spore preparations, e.g., microbial stabilizers, thickeners, hydrocolloids, pH buffers and the like. The composition may also include certain nutrient organic compounds, trace minerals, vitamins and growth factors. The concentration of these nutrient additives will depend on the type of additive and the plant and soil being treated but, in general, will be between about 0.01% and about 5% by weight of final liquid formulation.

The CFU/ml of spores in the formulated liquid concentrate is determined by doing a total spore count where the appropriate serial dilution is prepared by methods well known to those skilled in the art, and the final dilution is then subjected to 80° C. for 5 minutes, quenched in an ice bath, and then plated on standard Tryptic Soy Agar. After incubation at 37° C. for 18 to 24 hours, the colonies per plate are counted, and the spore count is calculated by multiplying the colonies per plate by the total dilution factor to obtain the CFU/ml in the formulated *Bacillus* concentrate liquid. Since each *Bacillus* strain has distinct and differentiable colony morphology, the individual *Bacillus* strains can be quantified in each *Bacillus* concentrate by counting the respective numbers of colony types on each plate.

Example 6

Formulation of a Dry Concentrate of Six *Bacillus* Strains

Spores from six (6) strains of *Bacillus* are grown in monoculture as described herein and the respective liquid concentrates are spray dried as described herein. An amount from each of the six *Bacillus* strain dry powder concentrates is weighed into powder blending equipment along with an inert powder carrier/diluent, and blended using a V-blender such that the desired final concentration of each *Bacillus* strain is attained. The equipment for powder mixing and blending can be any powder mixing equipment standard and known to one skilled in the art of powder blending and formulation, including but not limited to rotating blenders such as a V-Blender or a ribbon blender. Sufficient component inter-mixing must be attained to ensure a homogeneous blend. The final concentration for each of the *Bacillus* strain can range from $1 \times 10^6$ CFU/gm final powder up to $1 \times 10^{12}$ CFU/gm final powder but is more generally in the range of $1 \times 10^9$ CFU/gm final powder up to $1 \times 10^{11}$ CFU/gm final powder.

The composition of the powder/diluents can be any inert powdered diluent standard to one skilled in the art of powder formulations, any inert powdered diluent, dry additives and dry excipients that do not have a deleterious effect on the action of the spores, or any inert powdered diluent, additives and excipients and other ingredients conventionally used in powered spore preparations, e.g., anti-caking agents, flow agents, desiccants and the like. The composition may also include certain powdered nutrient organic compounds, trace minerals, vitamins and growth factors. The concentration of these nutrient additives will depend on the type of additive and the plant and soil being treated but, in general, will be between about 0.01% and about 5% by dry weight of final powder formulation.

The CFU/gm of spores in the formulated powder concentrate is determined by doing a total spore count where the appropriate serial dilution is prepared by methods well known to those skilled in the art, and the final dilution is then subjected to 80° C. for 5 minutes, quenched in an ice bath, and then plated on standard Tryptic Soy Agar. After incubation at 37° C. for 18 to 24 hours, the colonies per plate are counted, and the spore count is calculated by multiplying the colonies per plate by the total dilution factor to obtain the CFU/gram in the formulated *Bacillus* concentrate powder. Since each *Bacillus* strain has distinct and differentiable colony morphology, the individual *Bacillus* strains can be quantified in each *Bacillus* concentrate by counting the respective numbers of colony types on each plate.

Example 7

Application of *Bacillus* to Soybeans

Solution of *Bacillus* spores in liquid form and containing four strains of *Bacillus* containing a minimum of 250 million CFU/ml is applied at the rate of 1 gallon per acre through mechanical spraying apparatus commonly found on U.S. farms. The liquid suspension may be sprayed onto any typical row crop seeds such as soybeans, corn, wheat, maize directly into the furrow of soil onto the seed as it is planted. Spore concentrate may be applied simultaneously as the seed is deposited into the furrow. Concentration of spores can be adjusted as high as 5 billion CFU/mL, and dose applied to seeds at planting can be adjusted to as low as 32 fluid ounces per acre. Seeds treated in furrow should be conventional seeds with no additional materials added, such as pesticides, fertilizers and the like. Plants can be examined for evidence of fungal pathogens from time of germination through harvest. The pictures in FIGS. 7 and 8 demonstrate the effectiveness of the *Bacillus* blend acting in synergy with naturally occurring *Rhizobium* at developing nitrogen nodules on soybeans. No additional *Rhizobium* was added to the field, and the only treatment was addition of the *Bacillus* at time of planting the seeds.

Example 8

Application of *Bacillus* to Row Crops

Figure 7:
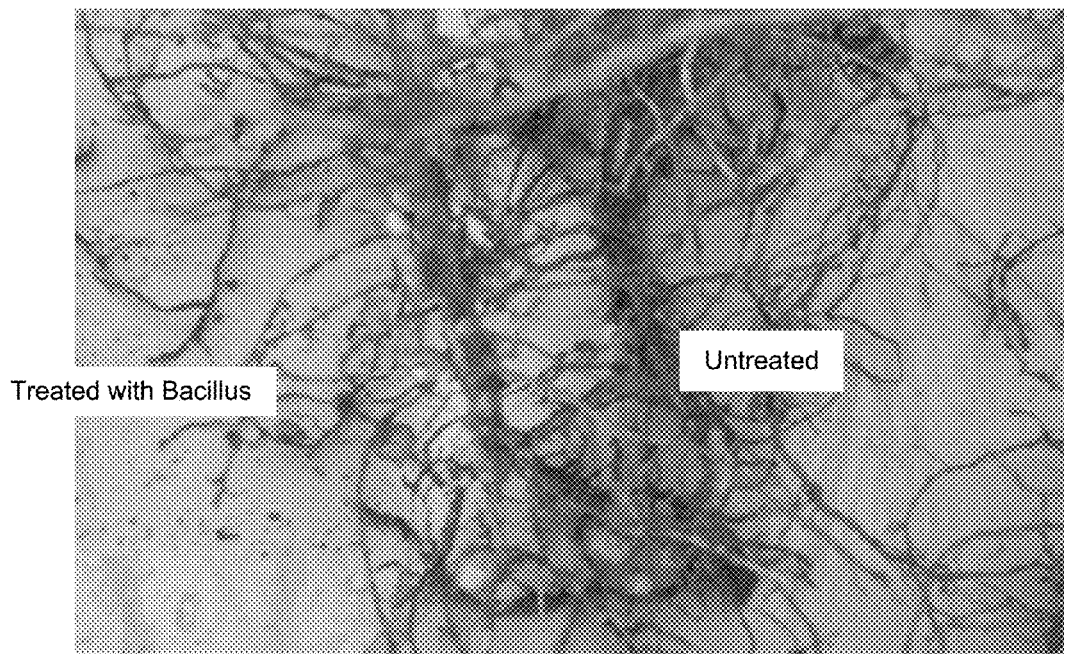
FIG. 7 depicts the roots of soybeans showing plants treated with *Bacillus* and plants not treated with *Bacillus*. The treated soybean plants show naturally occurring *Rhizobium* developing nitrogen nodules of greater number and larger size on the roots.
Figure 8:
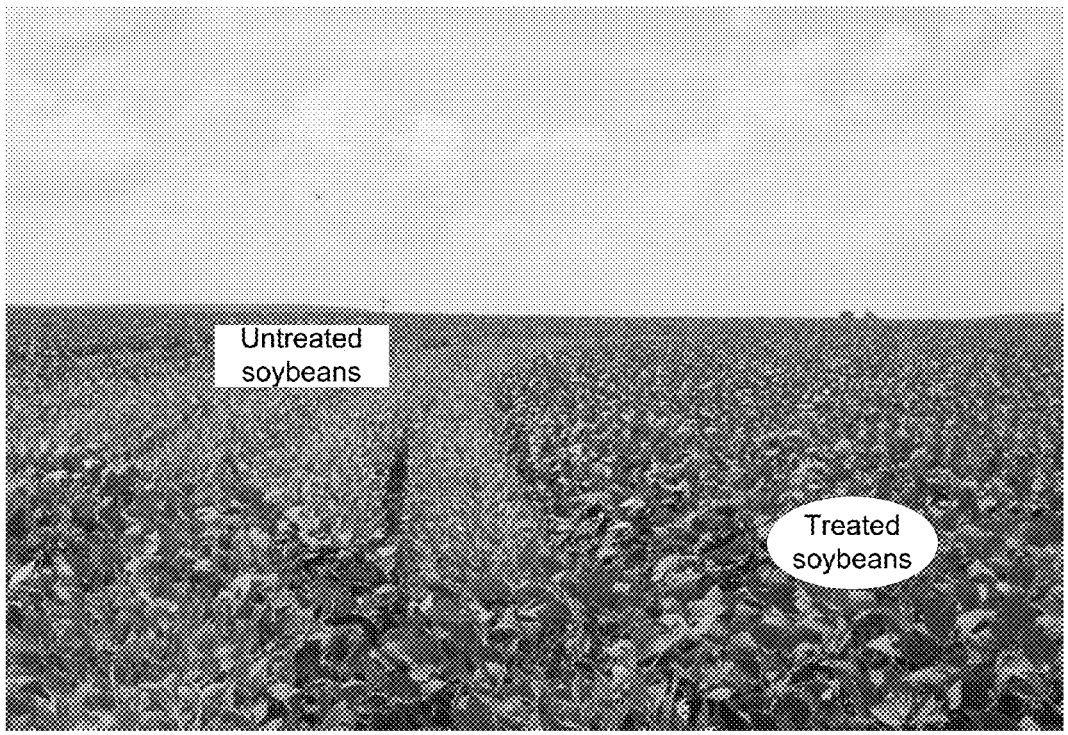
FIG. 8 is a photograph of rows of untreated (no *Bacillus*) soybeans compared to rows of treated soybeans (treated with *Bacillus*). The treated soybeans are larger plants with darker foliage.
Figure 9:
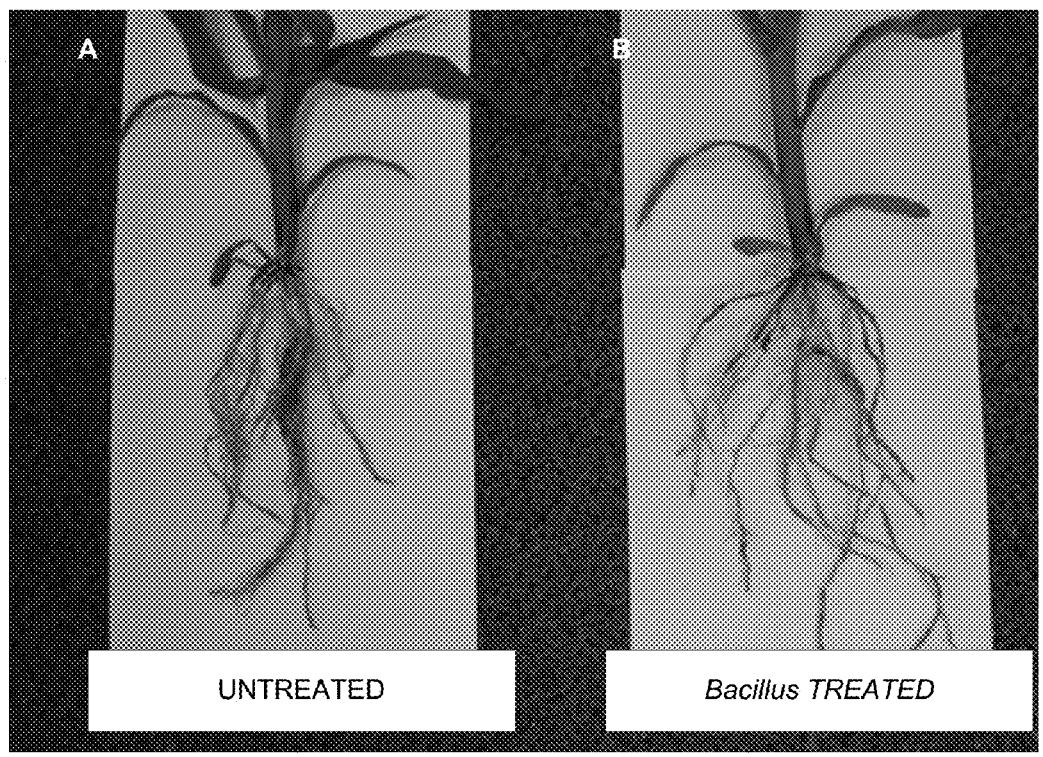
FIG. 9 is a photograph of corn stalks (4 weeks after germination) showing *Bacillus* treated on the right (B); untreated on left (A). The treated plant (B) shows a healthier root system than the untreated plant.

Solution of *Bacillus* spores (containing four strains) in dry form (spray dried) containing concentration of up to 500 billion per gram CFU's is dissolved in 50 to 250 gallons of water in typical liquid holding/spray vessels used on farms; material is slightly mixed to develop a liquid suspension. The liquid suspension may be sprayed onto any typical row crop seeds such as soybeans, corn, wheat, maize etc. directly into the furrow of soil onto the seed as it is planted. Spore concentrate may be applied simultaneously as the seed is deposited into the furrow. The rate of application can range from 1 gallon per acre to 100 milliliters per acre depending on level of pathogen control required. FIGS. 7 and 9 show the beneficial effects of *Bacillus* applied to soybeans and corn, respectively.

Example 9

Application of *Bacillus* by Seed Coating for Row Crops

A liquid suspension comprising four *Bacillus* strains and ranging in total CFU/ml of 50-100 billion CFU/ml may be applied directly to row crop seeds through any number of application methods as a coating and then dried to form a micro layer of dried *Bacillus* spores on the seed. Seeds are then planted per usual farming practices. Seed coating can be applied in a variety of ways including adding liquid spores to seed in a rotary drum type drying mechanism and rotated for 2-15 minutes to ensure adequate distribution; spores can be applied in a thin mist spray across a conveyor full of seeds and air dried to achieve coating effect or sprayed onto surface of seeds as one of multiple spray ports as seeds are passed through a rotating screw type conveyor. Final spore concentrate on seeds may range from 0.1 ounce per 50 pounds up to 2 fluid ounce per 50 pounds.

Example 10

Application of *Bacillus* to Row Crops by Foliar Spray

At first onset of visible pathogen infestation, liquid *Bacillus* spore concentrate containing 5-11 strains (250 million CFU/ml up to 5 billion CFU/ml) can be sprayed directly onto row crops as a foliar spray. Application rate can be varied to achieve a dose rate of anywhere from 1 gallon to 1 quart per acre. Higher concentrations of spores can be diluted in water to achieve a more uniform distribution. Concentrations of 50-100 billion CFU/ml can diluted in 50-250 gallons of water prior to spraying. Spraying as foliar application can be applied to many row crops such as soybeans, corn and wheat along with a wide variety of vegetable products such as tomatoes, peppers, beans, broccoli, cauliflower, cucumbers, zucchini, and eggplant. Foliar spray can also be applied to fruit shrubs and plants such as grapes, raspberries, strawberries, and blueberries.

Additionally, in cases of fruit trees such as apple, pear, peaches and the like, this same liquid concentrate or diluted with water can be applied to young and mature trees to prevent pathogen damage or to aid in the trees recovery from a pathogen infection

Example 11

Application of *Bacillus* to Fruit Trees or Bushes by Dipping

Figure 11:
FIG. 11 is a photograph of poplar trees three weeks after dip treatment with (B) and without *Bacillus* treatment (A).

New seedling fruit trees or bushes may be dipped into containers in which liquid spore concentrate has been added, either as a low active concentrate (250 million CFU/ml up to 5 billion CFU/ml) or high active concentrate diluted in water (50 to 100 billion CFU/ml; 8-32 fl oz into 3-5 gallons of water). Seedlings may be held for no more than 30 seconds in the solution then immediately planted. Within 7 days of planting, trees are treated a second time similar to what was outlined in Example 9. FIG. 11 shows the beneficial effect of *Bacillus* applied to poplar tree seedlings.

Example 12

Application of *Bacillus* to Ornamental Flowers

Figure 10:
FIG. 10 is a photograph of ornamental flowers showing *Bacillus* treated on the right (B); untreated on left (A). The treated plants in (B) show a larger plants with greater foliage than the untreated plant.

Liquid *Bacillus* spore concentrate at concentrations identical to those described in Example 4, 5 and 9 above is sprayed onto ornamental flowers (both annuals and perennials) such as geraniums, petunias, daffodils, either at germination of seeds or as foliar spray within 3-5 days of germination as preventive measure for pathogen occurrence. If pathogen infestation is detected prior to spraying, treatments should be repeated every day by suspending the spore concentrate into the nursery irrigation water so a low dose (100-200,000 CFU/ml is delivered each day through normal watering procedures. This treatment should continue for 7 days. FIG. 10 shows the effect on treated and untreated ornamental flowers.

Those skilled in the art will recognize, or be able to ascertain using no more than routine experimentation, many equivalents to the specific embodiments of the invention described herein. Such equivalents are intended to be encompassed by the following claims.

What is claimed is:

1. A composition comprising spray-dried *Bacillus amyloliquefaciens* BCM-CM5 (PTA-121388), spray-dried *Bacillus pumilus* NRRL-1875, and spray-dried *Bacillus subtilis* 10 DSM-10, and further comprising spray-dried *Brevibacillus laterosporus* strain CM-3 and/or spray-dried *Brevibacillus laterosporus* strain CM-33.

2. The composition of claim 1, wherein composition comprises spores or live cells of *Bacillus* strains.

3. The composition of claim 2, wherein the *Bacillus* strain bacteria are in spore form.

4. The composition of claim 1, wherein the composition further comprises nutrient organic compounds, trace minerals, vitamins, growth factors, and/or adjuvants.

5. The composition of claim 1, wherein each of the *Bacillus* strain bacteria is in a concentration of $1\times10^3$ to $1\times10^{12}$ colony forming units (CFU)/mL.

6. The composition of claim 1, wherein the composition is a powder.

7. A method for preparing the *Bacillus* strain composition of claim 1 comprising growing the *Bacillus* strain bacteria until the bacteria forms spores, and spray-drying the spores.

8. The composition of claim 1, wherein the composition further comprises at least one of the following *Bacillus lichenformis* ATCC-11946, *Bacillus mojavensis* BCM-01 (PTA-121389), *Bacillus pumilus* NRRL-1875, *Bacillus subtilis* NRRL-1650, *Bacillus megaterium* BCM-07 (PTA-121390), *Paenibacillus polymyxa* DSM-36, *Paenibacillus chitinolyticus* DSM-11030, or a combination thereof.

9. A method for inhibiting the growth and/or activity of fungal plant pathogens comprising applying the composition claim 1 to a plant, seed for a plant, or soil adjacent to a plant.

10. The method of claim 9, wherein the fungal plant pathogen is a member of the *Fusarium* species, optionally *Fusarium graminearum, Fusarium oxysporum, Fusarium solani, Fusarium verticilliodes*, and *Fusarium virgulforme; Phytophthora* species, optionally *Phytophthora medicaginis* and *Phytophthora sojae; Pythium* species, optionally *Pythium aphanidermatum* and *Pythium ultimum, Rhioctonia* species, optionally *Rhioctonia solani*; and *Sclerotinia* species, optionally *Sclerotinia sclerotiorum*.

11. The method of claim 9, wherein the composition is applied to the soil, to the plant foliage, to the plant seeds, during sowing of the plant seeds, or after the plants germinate.

12. The method of claim 9, wherein the composition is applied by spraying plants or mixing into soil.

13. The method of claim 9, wherein the composition is applied around the seed of the plant and/or to the root zone.

14. The method of claim 9, wherein the composition is applied within 2 weeks of plant emergence.

15. The method of claim 9, wherein the composition is applied after a fungal pathogen is present.

16. The method of claim 9, wherein the composition is applied by seed coating, spraying in planting furrow with seeds, or foliar spray.

17. A composition comprising spray-dried *Bacillus mojavensis* BCM 01 (PTA-121389), wherein said composition is a powder.

18. The composition of claim 17, further comprising spray-dried *Bacillus licheniformis* ATCC-11946.

19. The composition of claim 18, further comprising spray-dried *Brevibacillus laterosporus* strain CM-3 and/or *Brevibacillus laterosporus* strain CM-33.

20. The composition of claim 19, wherein each of the *Bacillus mojavensis* BCM 01 (PTA 121389), *Bacillus licheniformis* ATCC-11946, *Brevibacillus laterosporus* strain CM-3 and/or *Brevibacillus laterosporus* strain CM-33 are in a concentration of $1\times10^8$ to $1\times10^{12}$ colony forming units (CFU)/gram.

21. The composition of claim 18, wherein each of the *Bacillus mojavensis* BCM 01 (PTA 121389) and *Bacillus licheniformis* ATCC-11946 are in a concentration of $1\times10^8$ to $1\times10^{12}$ colony forming units (CFU)/gram.

22. The composition of claim 19, further comprising spray-dried *Bacillus amyloliquefaciens* BCM-CM5 (PTA-121388).

23. The composition of claim 22, wherein each of the *Bacillus mojavensis* BCM 01 (PTA 121389), *Bacillus licheniformis* ATCC-11946, *Brevibacillus laterosporus* strain CM-3 and/or *Brevibacillus laterosporus* strain CM-33, and *Bacillus amyloliquefaciens* BCM-CM5 (PTA-121388) are in a concentration of $1\times10^8$ to $1\times10^{12}$ colony forming units (CFU)/gram.

24. The composition of claim 17, wherein the *Bacillus mojavensis* BCM 01 (PTA 121389) is in a concentration of $1\times10^8$ to $1\times10^{12}$ colony forming units (CFU)/gram.

25. A method for preparing the composition of claim 17, comprising preparing *Bacillus mojavensis* BCM 01 (PTA-121389) spores and spray-drying the spores.

\* \* \* \* \*